(12) United States Patent
Li et al.

(10) Patent No.: US 8,778,948 B2
(45) Date of Patent: Jul. 15, 2014

(54) SUBSTITUTED PHENYLPIPERAZINYL ARALKYLALCOHOL DERIVATIVES, PHARMACEUTICAL COMPOSITIONS CONTAINING SUCH DERIVATIVES AND USES THEREOF

(75) Inventors: Jianqi Li, Xuzhou (CN); Guan Wang, Xuzhou (CN); Guisen Zhang, Xuzhou (CN); Xiangping Yang, Xuzhou (CN); Peng Xie, Xuzhou (CN); Linjie Zhang, Xuzhou (CN); Xiangqing Xu, Xuzhou (CN); Yumei Wang, Xuzhou (CN)

(73) Assignee: NHWA Pharma, Corporation, Xuzhou, Jiangsu (CN)

( * ) Notice: Subject to any disclaimer, the term of this patent is extended or adjusted under 35 U.S.C. 154(b) by 251 days.

(21) Appl. No.: 13/141,803

(22) PCT Filed: Dec. 22, 2009

(86) PCT No.: PCT/CN2009/075836
§ 371 (c)(1),
(2), (4) Date: Aug. 17, 2011

(87) PCT Pub. No.: WO2010/072144
PCT Pub. Date: Jul. 1, 2010

(65) Prior Publication Data
US 2011/0294822 A1    Dec. 1, 2011

(30) Foreign Application Priority Data

Dec. 23, 2008 (CN) .......................... 2008 1 0207609

(51) Int. Cl.
| | | |
|---|---|---|
| A61K 31/495 | (2006.01) | |
| A61K 31/496 | (2006.01) | |
| C07D 295/088 | (2006.01) | |
| C07D 403/08 | (2006.01) | |
| C07D 417/08 | (2006.01) | |

(52) U.S. Cl.
USPC ............ 514/254.02; 514/254.06; 514/254.09; 514/255.03; 544/368; 544/370; 544/373; 544/393; 544/394

(58) Field of Classification Search
None
See application file for complete search history.

(56) References Cited

U.S. PATENT DOCUMENTS

| | | | | |
|---|---|---|---|---|
| 4,474,977 A | * | 10/1984 | Lambelin et al. | 560/1 |
| 4,587,248 A | * | 5/1986 | Cantarelli et al. | 514/252.12 |
| 4,960,778 A | | 10/1990 | Lesieur et al. | |
| 5,104,438 A | * | 4/1992 | Seele et al. | 504/272 |
| 6,232,314 B1 | | 5/2001 | Jarrott et al. | |
| 7,576,086 B2 | * | 8/2009 | Li et al. | 514/252.13 |
| 2005/0267121 A1 | * | 12/2005 | Li et al. | 514/252.12 |

FOREIGN PATENT DOCUMENTS

| | | |
|---|---|---|
| GB | 1097572 A | 1/1968 |
| JP | 51141829 A | 12/1976 |
| JP | 53059675 A | 5/1978 |
| WO | WO 8201186 A1 | 4/1982 |

OTHER PUBLICATIONS

Chen et al. European Journal of Medicinal Chemistry 44, pp. 4367-4375 (2009).*
International Search Report for PCT/CN2009/075836 mailed Apr. 1, 2010.
Ortiz, Aurelio et al., "A new method for the preparation of unsymmetrical 1,4-substituted piperazine derivatives.", Tetrahedron: Asymmetry 1999, vol. 10, No. 4, pp. 799-811, ISSN 0957-4166.
Bonte, J.P. et al., "Amino ketone and amino alcohol derivatives of benzoxazolinone: synthesis, adrenergic and antihypertensive properties", Eur J Med Chem 1990, vol. 25, No. 4, pp. 361-368, ISSN 0223-5234.

* cited by examiner

*Primary Examiner* — Emily Bernhardt
(74) *Attorney, Agent, or Firm* — Swanson & Bratschun, LLC

(57) ABSTRACT

The invention relates to a substituted phenylpiperazine aryl alkanol derivative represented by the following general formula and its salt and hydrate,

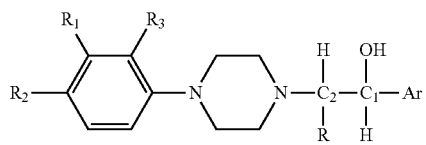

wherein $C_1$ and $C_2$ represent chiral carbon atoms, and the compound is one of the six isomers: (1RS, 2SR), (1RS, 2RS), (1R, 2S), (1S, 2S), (1R, 2R) or (1S, 2R); and R, $R_1$, $R_2$, $R_3$ and Ar are as defined in the specification. The derivative is non-opioid analgesic, has good analgesic effect and relatively small side effects. The invention also relates to a composition comprising the derivative and its use.

13 Claims, No Drawings

SUBSTITUTED PHENYLPIPERAZINYL ARALKYLALCOHOL DERIVATIVES, PHARMACEUTICAL COMPOSITIONS CONTAINING SUCH DERIVATIVES AND USES THEREOF

RELATED APPLICATIONS

This application is a 35 U.S.C. §371 national phase application of PCT/CN2009/075836 (WO 2010/072144), filed on Dec. 22, 2009, entitled "Substituted Phenylpiperazinyl Aralkylalcohol Derivatives, Pharmaceutical Compositions Containing Such Derivatives and Uses Thereof," which application claims the benefit of Chinese Application No. 200810207609.0, filed Dec. 23, 2008, which is incorporated herein by reference in its entirety.

FIELD OF THE INVENTION

This invention relates to a novel substituted phenylpiperazine aryl alkanol derivative and its use in preparing analgesic drugs.

BACKGROUND OF THE INVENTION

Severe acute and chronic pains refer to the nociception and painful sensation resulted from stimulation of nociceptors by a variety of injury stimuli passed to the central nervous system by the impulse of messenger of nociceptive transmission. Severe acute and chronic pains, including cancer pains, post-operative pains, a variety of repeated episodes of acute and chronic pains, trouble tens of millions of patients, and constitute a major clinical problem.

Clinical analgesics can be divided into three categories: 1) non-steroidal anti-inflammatory analgesic, 2) opioid analgesics, and 3) other non-opioid analgesics, including local anesthetics, anti-depressants, antiepileptic drugs, etc.

Currently, acute pains and cancer pains are mainly treated with opioid analgesics clinically. Broad application of opioid analgesic drug is limited due to its side effects such as addiction, respiratory depression and reduced gastric movement. Treatment of a variety of chronic non-cancer pains and neuropathic pains with opioid analgesics or non-steroidal anti-inflammatory drugs is hardly satisfying. Therefore, the search of broad-spectrum analgesic drugs having a strong analgesic effect while overcoming many side effects of opioid and non-steroidal anti-inflammatory analgesic drugs has become the primary goal of the field and the focus of innovative pharmaceutical research.

In recent years, some large pharmaceutical companies abroad, such as Merck and Pfizer, etc., have invested heavily in the development of new non-narcotic central analgesics, and have made some progress. For example, in 2005 the U.S. FDA approved the listing of calcium channel blocker Ziconotide for the treatment of severe chronic pains that cannot be treated with or is tolerated by other drugs. This drug can lead to side effects such as orthostatic hypotension.

Existing drugs are far from meeting the clinical needs of pain control for different patients. Especially for certain types of cancer pains, severe chronic pains, and some neuropathic pains, there exists no suitable, safe and effective analgesic drug. Thus, development of non-narcotic analgesics with novel chemical structure having mild or no side effects, broad application, and clinical safety, continues, in order to meet the needs of different patients with pain. Meanwhile, non-opioid analgesics have a huge growing market and, if novel analgesics come out, they will have large social and economic benefits.

SUMMARY OF THE INVENTION

An object of the invention is to provide a substituted phenylpiperazine aryl alkanol derivative, which overcomes side effects of existing drugs, such as addiction, respiratory depression and reduced gastric motility, and solves clinical problems.

According to one aspect of the invention, there is provided a substituted phenylpiperazine aryl alkanol derivative having the following general formula,

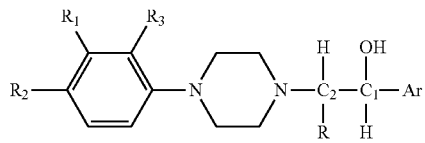

wherein:
$R$ represents $C_1$-$C_6$ alkyl unsubstituted or substituted with halogen, amino or hydroxyl;
$R_1$, $R_2$, and $R_3$ each represent H, halogen, hydroxyl, unsubstituted or halogen-substituted $C_1$-$C_4$ alkyl, or unsubstituted or halogen-substituted $C_1$-$C_4$ alkoxy, with a proviso that $R_1$, $R_2$, and $R_3$ are not simultaneously H;
Ar represents one of the following groups:

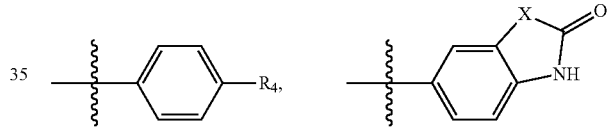

wherein:
$R_4$ represents H, halogen, hydroxyl, unsubstituted or halogen-substituted $C_1$-$C_4$ alkyl, unsubstituted or halogen-substituted $C_1$-$C_4$ alkoxy, —NHCO($C_1$-$C_4$ alkyl), —NHSO$_2$($C_1$-$C_4$ alkyl) or —NHSO($C_1$-$C_4$ alkyl);
X represents CH$_2$, S or NH,
with a proviso that: $C_1$ and $C_2$ in the general formula represent chiral carbon atoms, and the compound is one of the six (1RS, 2SR), (1RS, 2RS), (1R, 2S), (1S, 2S), (1R, 2R), and (1S, 2R) isomers; and salt and hydrate thereof.

According to another aspect of the invention, there is provided a pharmaceutical composition comprising the substituted phenylpiperazine aryl alkanol derivative according to the invention or its enantiomer, salt, or hydrate, and a pharmaceutically acceptable carrier.

According to still another aspect of the invention, there is provided the use of the substituted phenylpiperazine aryl alkanol derivative according to the invention or its enantiomer, salt, or hydrate in the preparation of analgesics.

According to yet another aspect of the invention, there is provided a method of treating mammals with pain, comprising administration of the substituted phenylpiperazine aryl alkanol derivative according to the invention, its enantiomer, salt or hydrate to individuals.

DETAILED DESCRIPTION OF THE INVENTION

In the invention, the terms "$C_1$-$C_4$ alkyl" and "$C_1$-$C_6$ alkyl" refers, respectively, to branched or linear alkyl having 1-4 or 1-6 carbon atoms, such as methyl, ethyl, n-propyl, isopropyl, n-butyl, isobutyl, tert-butyl, n-pentyl and n-hexyl.

The term "$C_1$-$C_4$ alkoxy" refers to —O—$C_1$-$C_4$ alkyl, wherein $C_1$-$C_4$ alkyl is as defined above.

In the context of the invention, the term "halogen" refers to fluorine, chlorine, bromine or iodine atoms.

In the invention, the term "mammal" includes human being.

The substituted phenylpiperazine aryl alkanol derivative according to the invention is a compound having the following general formula:

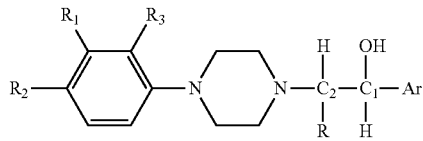

wherein, $C_1$ and $C_2$ represent chiral carbon atoms, and the compound is one of the six (1RS, 2SR), (1RS, 2RS), (1R, 2S), (1S, 2S), (1R, 2R) and (1S, 2R) isomers; and R, $R_1$, $R_2$, $R_3$ and Ar are as defined above.

In one embodiment of the substituted phenylpiperazine aryl alkanol derivative according to the invention, R represents $C_1$-$C_6$ alkyl unsubstituted or substituted with halogen, amino or hydroxyl. Preferably, R represents unsubstituted or halogen substituted $C_1$-$C_4$ alkyl, preferably unsubstituted or fluorine substituted $C_1$-$C_4$ alkyl, more preferably unsubstituted $C_1$-$C_4$ alkyl, such as methyl, ethyl, n-propyl and n-butyl.

In one embodiment of the substituted phenylpiperazine aryl alkanol derivative according to the invention, $R_1$, $R_2$, and $R_3$ each represent halogen, preferably fluorine or chlorine, more preferably chlorine. $R_1$, $R_2$, and $R_3$ may also each represent unsubstituted or halogen substituted $C_1$-$C_4$ alkyl, preferably unsubstituted or fluorine substituted $C_1$-$C_4$ alkyl, more preferably methyl or trifluoromethyl. In addition, $R_1$, $R_2$, and $R_3$ may also represent unsubstituted $C_1$-$C_4$ alkoxy, preferably methoxy.

In the substituted phenylpiperazine aryl alkanol derivative according to the invention, Ar represents one of the following groups:

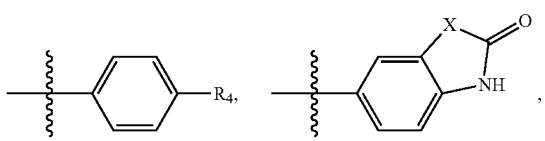

wherein:

$R_4$ represents H, halogen, hydroxyl, unsubstituted or halogen substituted $C_1$-$C_4$ alkyl, unsubstituted or halogen substituted $C_1$-$C_4$ alkoxy, —NHCO($C_1$-$C_4$ alkyl), —NHSO$_2$($C_1$-$C_4$ alkyl) or —NHSO($C_1$-$C_4$ alkyl); and X represents $CH_2$, S or NH.

According to one embodiment of the invention, $R_4$ represents H, halogen, hydroxyl, $C_1$-$C_4$ alkyl, $C_1$-$C_4$ alkoxy, —NHCO($C_1$-$C_4$ alkyl), —NHSO$_2$($C_1$-$C_4$ alkyl) or —NHSO ($C_1$-$C_4$ alkyl). According to another embodiment of the invention, $R_4$ represents H, fluorine, hydroxyl, methoxy, ethoxy, trifluoromethoxy, —NHCOCH$_3$, —NHSO$_2$CH$_3$ or —NHSOCH$_3$.

The compound according to the invention can be applied in the form of free base or pharmacologically acceptable salt or hydrate thereof. The salt can be acid addition salt, for example, formed by a suitable inorganic or organic acid. Examples of suitable inorganic acid include hydrohalogenic acid, such as hydrochloric acid, sulfuric acid, hydrobromic acid, trifluoroacetic acid and phosphoric acid. Examples of suitable organic acid include carboxylic acid, phosphonic acid, sulfonic acid or aminosulfonic acid, such as acetic acid, propionic acid, octanoic acid, decanoic acid, dodecanoic acid, glycolic acid, lactic acid, 2-hydroxybutyric acid, gluconic acid, glucose monocarboxylic acid, fumaric acid, succinic acid, adipic acid, pimelic acid, octanedioic acid, azelaic acid, malic acid, tartaric acid, citric acid, glucaric acid, galactaric acid; amino acids, such as glutamic acid, aspartic acid, N-methyl glycine, acetyl aminoacetic acid, N-acetyl-asparagine and N-acetyl cysteine; pyruvic acid, acetoacetic acid, phosphoserine, 2- or 3-glycerophosphoric acid, glucose-6-phosphate, glucose-1-phosphate, fructose-1,6-bisphosphate, maleic acid, hydroxymaleic acid, methyl maleic acid, cyclohexane carboxylic acid, adamantane carboxylic acid, benzoic acid, salicylic acid, 1- or 3-hydroxy-naphthyl-2-carboxylic acid, 3,4,5-trimethoxy benzoic acid, 2-phenoxy benzoic acid, 2-acetoxy benzoic acid, 4-amino salicylic acid, phthalic acid, phenylacetic acid, phenylhydroxy acetic acid, cinnamic acid, glucuronic acid, galacturonic acid, methanesulfonic acid or ethanesulfonic acid, 2-hydroxy ethanesulfonic acid, ethane-1,2-disulfonic acid, 2-, 3- or 4-methyl benzene sulfonic acid, methyl sulfuric acid, ethyl sulfuric acid, lauryl sulfuric acid, methanesulfonic acid, N-cyclohexylamino sulfonic acid, N-methyl, N-ethyl, or N-propyl amino sulfonic acid, or other organic acids, such as ascorbic acid. The salts are preferably hydrochloride, hydrobromide, sulfate, trifluoroacetate or methanesulfonate.

According to one embodiment of the invention, the salt contains 0.5-3 molecules of crystal water per molecule.

According to the invention, the substituted phenylpiperazine aryl alkanol derivative is a compound selected from the group consisting of the following, or a salt and a hydrate thereof:

I-1 (1RS,2SR)-1-phenyl-2-(4-(3-trifluoromethylphenyl)piperazinyl)-propan-1-ol,
I-2 (1RS,2RS)-1-phenyl-2-(4-(3-trifluoromethylphenyl)piperazinyl)-propan-1-ol,
I-3 (1RS,2SR)-1-phenyl-2-(4-(3-chlorophenyl)piperazinyl)-propan-1-ol,
I-4 (1RS,2RS)-1-phenyl-2-(4-(3-chlorophenyl)piperazinyl)-propan-1-ol,
I-5 (1RS,2SR)-1-phenyl-2-(4-(2,3-dimethylphenyl)piperazinyl)-propan-1-ol,
I-6 (1RS,2RS)-1-phenyl-2-(4-(2,3-dimethylphenyl)piperazinyl)-propan-1-ol,
I-7 (1RS,2SR)-1-phenyl-2-(4-(4-methoxyphenyl)piperazinyl)-propan-1-ol,
I-8 (1RS,2RS)-1-phenyl-2-(4-(4-methoxyphenyl)piperazinyl)-propan-1-ol,
I-9 (1RS,2SR)-1-phenyl-2-(4-(3-methoxyphenyl)piperazinyl)-propan-1-ol,
I-10 (1RS,2RS)-1-phenyl-2-(4-(3-methoxyphenyl)piperazinyl)-propan-1-ol,
I-11 (1RS,2SR)-1-(4-fluorophenyl)-2-(4-(2-methoxyphenyl)piperazinyl)-propan-1-ol,
I-12 (1RS,2RS)-1-(4-fluorophenyl)-2-(4-(2-methoxyphenyl)piperazinyl)-propan-1-ol,
I-13 (1RS,2SR)-1-(4-methoxyphenyl)-2-(4-(2-methoxyphenyl)piperazinyl)-propan-1-ol,
I-14 (1RS,2RS)-1-(4-methoxyphenyl)-2-(4-(2-methoxyphenyl)piperazinyl)-propan-1-ol,
I-15 (1RS,2SR)-1-(4-acetylaminophenyl)-2-(4-(3-trifluoromethylphenyl)piperazinyl)-propan-1-ol, I-16 (1RS,2RS)-1-(4-acetylaminophenyl)-2-(4-(3-trifluoromethylphenyl)piperazinyl)-propan-1-ol,
I-17 (1RS,2SR)-1-(4-methanesulfonamido phenyl)-2-(4-(3-trifluoromethylphenyl)piperazinyl)-propan-1-ol,
I-18 (1RS,2RS)-1-(4-methanesulfonamido phenyl)-2-(4-(3-trifluoromethylphenyl)piperazinyl)-propan-1-ol,
I-19 (1RS,2SR)-1-phenyl-2-(4-(2-methoxyphenyl)piperazinyl)-propan-1-ol,
I-20 (1RS,2RS)-1-phenyl-2-(4-(2-methoxyphenyl)piperazinyl)-propan-1-ol,
I-21 (1RS,2SR)-1-phenyl-2-(4-(2-methoxyphenyl)piperazinyl)-butan-1-ol,
I-22 (1RS,2RS)-1-phenyl-2-(4-(2-methoxyphenyl)piperazinyl)-butan-1-ol,
I-23 (1RS,2SR)-1-phenyl-2-(4-(2-methoxyphenyl)piperazinyl)-pentan-1-ol,
I-24 (1RS,2RS)-1-phenyl-2-(4-(2-methoxyphenyl)piperazinyl)-pentan-1-ol,
I-25 (1RS,2SR)-1-phenyl-2-(4-(2-methoxyphenyl)piperazinyl)-hexan-1-ol,
I-26 (1RS,2RS)-1-phenyl-2-(4-(2-methoxyphenyl)piperazinyl)-hexan-1-ol,
II-1 (1R,2S)-1-phenyl-2-(4-(2-methoxyphenyl)piperazinyl)-propan-1-ol,
II-2 (1S,2S)-1-phenyl-2-(4-(2-methoxyphenyl)piperazinyl)-propan-1-ol,
III-1 (1S,2R)-1-phenyl-2-(4-(2-methoxyphenyl)piperazinyl)-propan-1-ol,
III-2 (1R,2R)-1-phenyl-2-(4-(2-methoxyphenyl)piperazinyl)-propan-1-ol,
IV-1 (1RS,2SR)-5-(1-hydroxy-2-(4-(2-methoxyphenyl)piperazin-1-yl)propyl)indolin-2-one,
IV-2 (1RS,2RS)-5-(1-hydroxy-2-(4-(2-methoxyphenyl)piperazin-1-yl)propyl)indolin-2-one
IV-3 (1RS,2SR)-5-(1-hydroxy-2-(4-(2-methoxyphenyl)piperazin-1-yl)propyl)-1H-benzo[d]imidazol-2(3H)-one,
IV-4 (1RS,2RS)-5-(1-hydroxy-2-(4-(2-methoxyphenyl)piperazin-1-yl)propyl)-1H-benzo[d]imidazol-2(3H)-one,
IV-5 (1RS,2SR)-6-(1-hydroxy-2-(4-(3-(trifluoromethyl)phenyl)piperazin-1-yl)propyl)benzo[d]thiazol-2(3H)-one, and
IV-6 (1RS,2RS)-6-(1-hydroxy-2-(4-(3-(trifluoromethyl)phenyl)piperazin-1-yl)propyl)benzo[d]thiazol-2(3H)-one.

The structural formula of the above compounds are shown in Table 1:

| Code | Structual Formula |
|---|---|
| -1 | 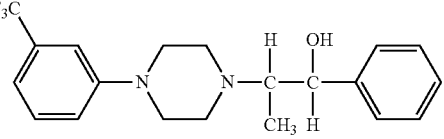 (1RS,2SR) |
| -2 | 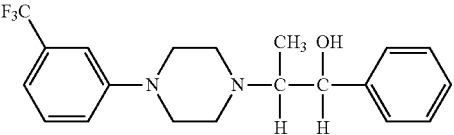 (1RS,2RS) |
| -3 | 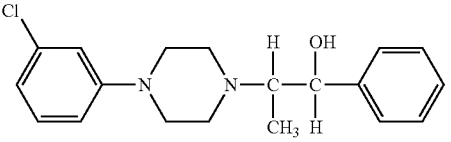 (1RS,2SR) |
| -4 | 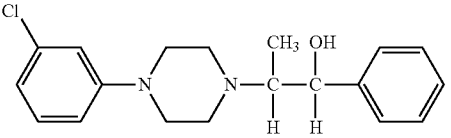 (1RS,2RS) |
| -5 | 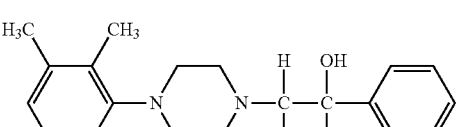 (1RS,2SR) |

-continued
| Code | Structural Formula |
|---|---|
| -6 | 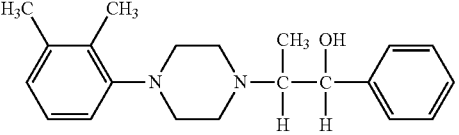<br>(1RS,2RS) |
| -7 | 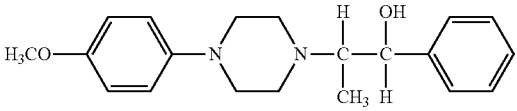<br>(1RS,2SR) |
| -8 | 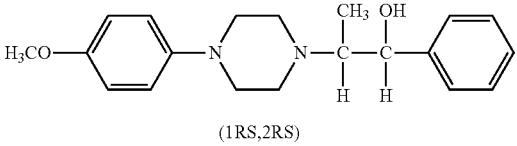<br>(1RS,2RS) |
| -9 | 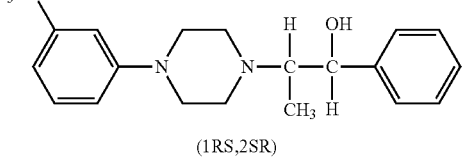<br>(1RS,2SR) |
| -10 | 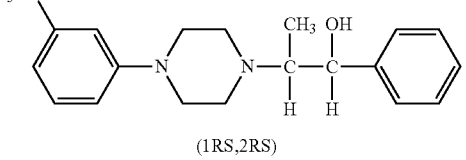<br>(1RS,2RS) |
| -11 | 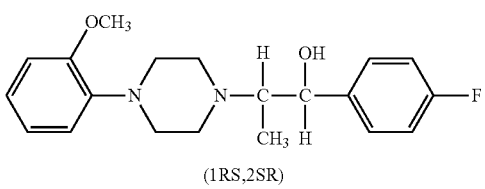<br>(1RS,2SR) |
| -12 | 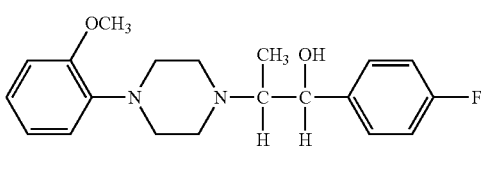<br>(1RS,2RS) |
| -13 | 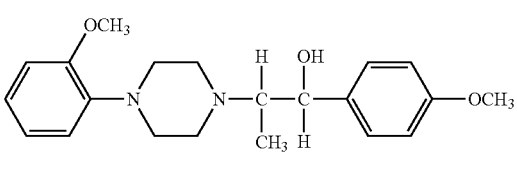<br>(1RS,2SR) |

-continued
| Code | Structural Formula |
|---|---|
| -14 | 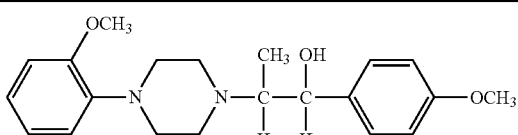 (1RS,2RS) |
| -15 | 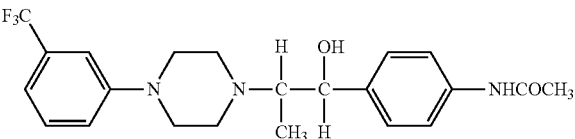 (1RS,2SR) |
| -16 | 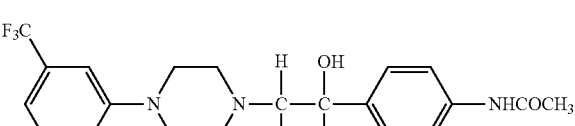 (1RS,2RS) |
| -17 | 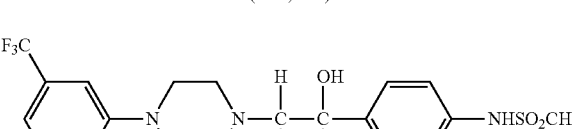 (1RS,2SR) |
| -18 | 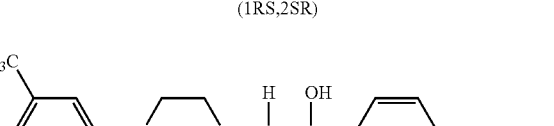 (1RS,2RS) |
| -19 | 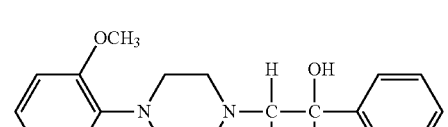 (1RS,2SR) |
| -20 | 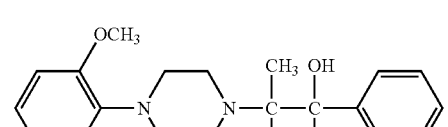 (1RS,2RS) |
| -21 | 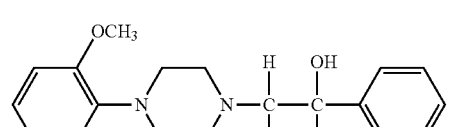 (1RS,2SR) |

-continued
| Code | Structural Formula |
|---|---|
| -22 | 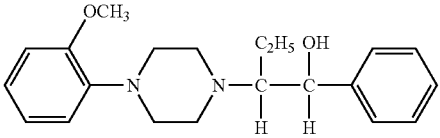<br>(1RS,2RS) |
| -23 | (1RS,2SR) |
| -24 | (1RS,2RS) |
| -25 | (1RS,2SR) |
| -26 | (1RS,2RS) |
| -1 | (1R,2S) |
| -2 | (1S,2S) |
| -1 | (1S,2R) |

-continued
| Code | Structural Formula |
|---|---|
| -2 | 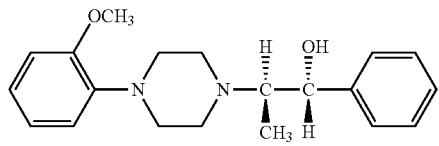<br>(1R,2R) |
| -1 | 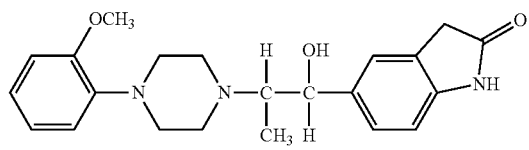<br>(1RS,2SR) |
| -2 | 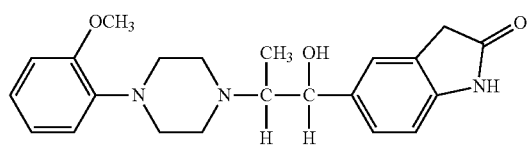<br>(1RS,2RS) |
| -3 | 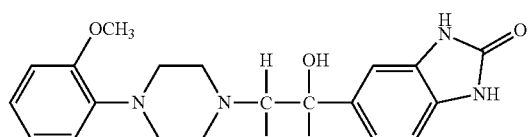<br>(1RS,2SR) |
| -4 | 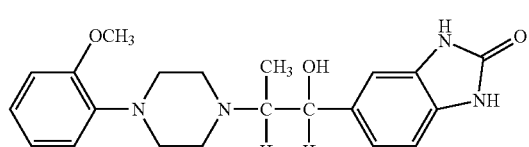<br>(1RS,2RS) |
| -5 | 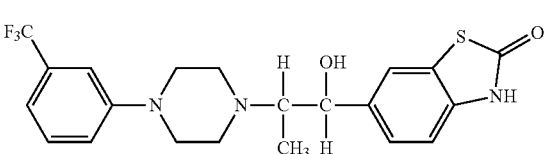<br>(1RS,2SR) |
| -6 | 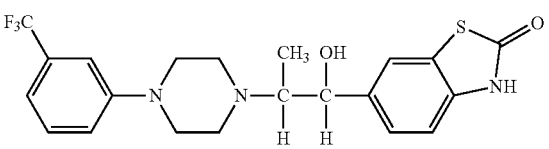<br>(1RS,2RS) |

Among the above compounds, the compound selected from the group consists of:

I-1 (1RS,2SR)-1-phenyl-2-(4-(3-trifluoromethylphenyl)piperazinyl)-propan-1-ol,
I-13 (1RS,2SR)-1-(4-methoxyphenyl)-2-(4-(2-methoxyphenyl)piperazinyl)-propan-1-ol,
I-20 (1RS,2RS)-1-phenyl-2-(4-(2-methoxyphenyl)piperazinyl)-propan-1-ol, and
III-2 (1R,2R)-1-phenyl-2-(4-(2-methoxyphenyl)piperazinyl)-propan-1-ol, or a salt and a hydrate thereof is preferred.

The compound of the invention can be synthesized by the following methods: Synthetic route one:

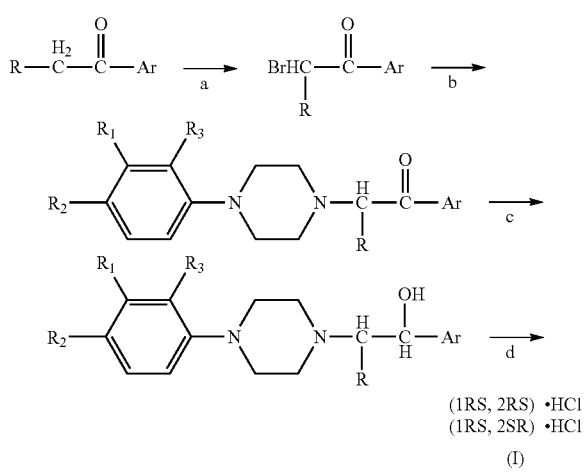

a. CuBr₂, CHCl₃, EtOA
b. CH₃COCH₃, K₂CO₃
c. NaBH4, C₂H₅OH
d. 1) Al₂O₃ column chromatography,
   2) HCl/C₂H₅OH
Ar. benzene or substituted benzene
R: CH₃, C₂H₅, C₃H₇, C₄H₉
R₁: H, Cl, CH₃O, CF₃
R₂: H, CH₃O
R₃: H, CH₃O, CH₃

An aryl alkanone, used as a starting material, is subjected to α-bromination reaction with copper bromide, giving a corresponding α-brominated aryl alkanone, which undergoes condensation reaction with a substituted phenylpiperazine. Subsequent reduction gives the target compound (I).

By the method of synthetic route one, the target compounds I-1 to I-26 can be obtained.

General guideline of synthetic route one (hereinafter abbreviated as general procedure A):

Preparation of (1RS,2SR)-1-substituted phenyl-2-(4-substituted phenyl-piperazinyl)alkyl-1-alcohol(I) hydrochloride and (1RS,2RS)-1-substituted phenyl-2-(4-substituted phenyl-piperazinyl)alkyl-1-alcohol (I) hydrochloride 1) Preparation of 2-bromo-1-phenyl alkanone 0.1 mol of phenyl alkanone is dissolved in 200 ml mixture of chloroform and ethyl acetate (volume ratio 1:1), and 0.2 mol of solid copper bromide is added under stirring at room temperature. A reaction is allowed to proceed under refluxing for 12 hours. The reaction mixture is cooled to room temperature, and filtered. The filtrate is concentrated to dry. The remaining oily product is extracted with petroleum ether (2×100 ml) with heating. Insoluble substance is removed, and the petroleum ether phases are combined, and evaporated to give oily product. The oily product is cooled and crystallized, to produce 2-bromo-1-phenyl alkanone. The yield is 75 to 90%.

2) Preparation of 1-substituted phenyl-4-benzoyl alkyl piperazine hydrochloride

The substituted phenyl piperazine (0.01 mol) and 2-bromo-1-phenyl alkanone (0.012 mol) are dissolved in 50 ml of acetone, and anhydrous potassium carbonate (4.15 g, 0.03 mol), and potassium iodide (0.15 g, 1.0 mmol) are added. A reaction under refluxing is allowed to proceed at an elevated temperature for 5 hours. The reaction solution is cooled, and filtered. The filtrate is evaporated to dry, added to 150 ml ethyl acetate, and washed with water (1×50 ml) and saturated brine (1×50 ml), dried and filterer. The pH of the filtrate is adjusted with HCl/C₂H₅OH(5N) to 2. The resulting solid precipitate is filtered, and recrystallized with ethanol/water or ethanol/ethyl acetate, to produce 1-aralkyl-4-benzoyl alkyl piperazine hydrochloride. The yield is 80 to 90%.

3) Preparation of (1RS,2SR) and (1RS,2RS)-1-substituted phenyl-2-(4-substituted phenyl piperazinyl) alkyl-1-alcohol(I) hydrochloride 1-aralkyl-4-benzoyl alkyl piperazine hydrochloride (4.0 mmol) is dissolved in 30 ml methanol, and sodium borohydride (8.4 mmol) is added in proportions, mixed and stirred at room temperature till completion of the reaction. The reaction mixture is cooled in ice water, adjusted to pH of 4 by dropwise addition of 3N hydrochloric acid at a controlled temperature of <20, stirred for 0.5 hours, and then neutralized with saturated sodium bicarbonate solution. 10 ml of water is added, and methanol is removed by rotary evaporation. The mixtured is adjusted to pH of 10 with 10% (w/w) NaOH solution, and extracted with ethyl acetate (2×20 ml). The organic phases are combined, washed with 20 ml of saturated brine, dried with anhydrous magnesium sulfate, filtered, and evaporated till dry to remove ethyl acetate, to obtain oily product. The oily product is purified by column chromatography (neutral Al₂O₃), and eluted with dichloromethane, to obtain threoisomer and erythroisomer. The obtained threoisomer and erythroisomer are separately dissolved in an appropriate amount of ethyl acetate, and adjusted to pH of 2 with HCl/C₂H₅OH (5N). The resulting solid precipitate is filtered, and recrystallized with ethanol/water or ethanol/ethyl acetate, to respectively obtain (1RS,2SR)-1-substituted phenyl-2-(4-substituted phenyl piperazinyl)alkyl-1-alcohol (I) hydrochloride, with a yield of 25~35%; and (1RS,2RS)-1-substituted phenyl-2-(4-substituted phenyl piperazinyl)alkyl-1-alcohol (I) hydrochloride, with a yield of 25~35%.

Synthetic Route Two:

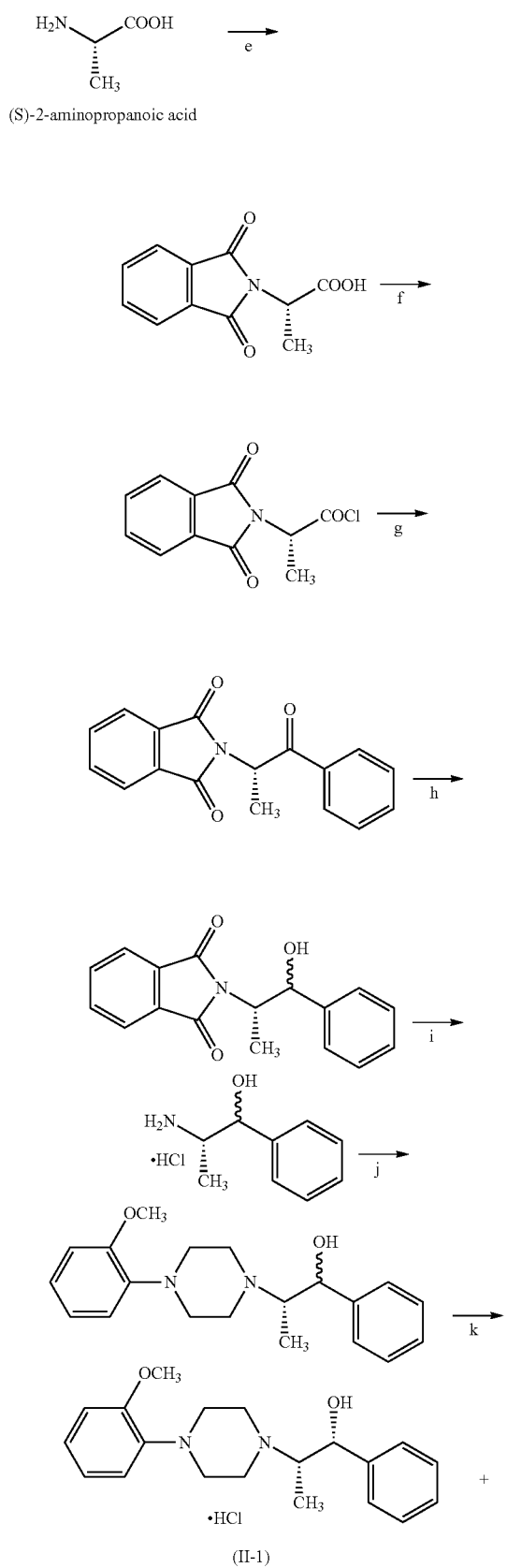

(II-1)

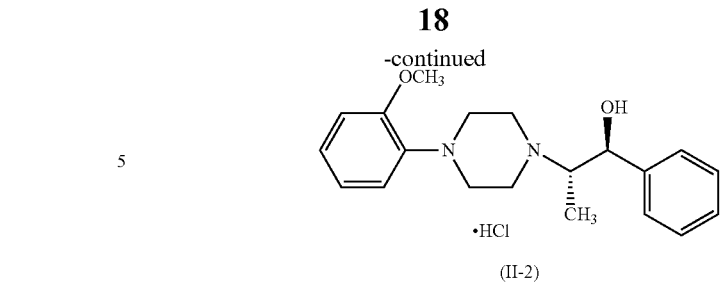

(II-2)

e. Phthalic anhydride, CH$_3$OH
f. Pyridine, ClCOCOCl, CH$_2$Cl$_2$
g. AlCl$_3$, Benzene/CH$_2$Cl$_2$
h. Al(i-PrOH)$_3$/PrOH, Toluene
i. NH$_2$NH$_2$/H$_2$O
j. CH$_3$CN, Et$_3$N
k. Al$_2$O$_3$, HCl/C$_2$H$_5$OH S-2-amino-propionic acid, used as a starting material, is first reacted with phthalic anhydride to protect the amino group, then reacted with oxalic acid to prepare the corresponding acyl chloride. The acyl chloride is subjected to Friedel-Crafts acylation reaction with benzene in the presence of aluminium chloride, reduction with aluminium isopropoxide, deprotection, and cyclization with aryl nitrogen mustard. Subsequent purification by neutral alumina chromatography gives the target compound (II).

By the method of synthetic route two, the target compounds II-1 and II-2 can be obtained.

Synthetic Route Three:

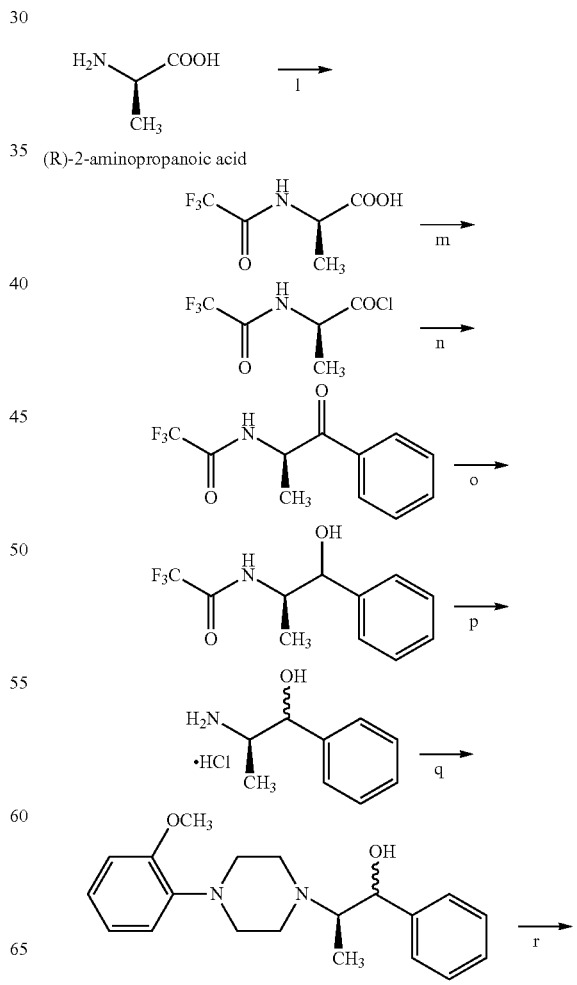

-continued

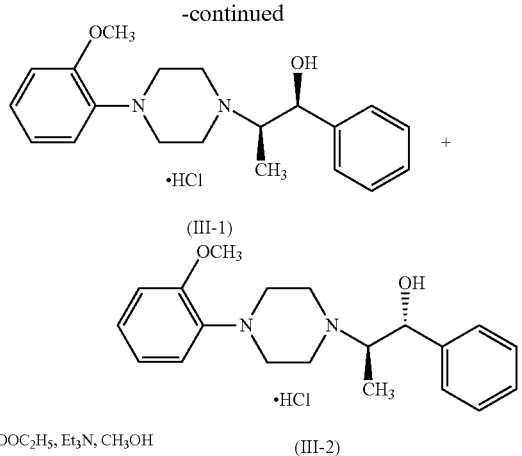

1. CF₃COOC₂H₅, Et₃N, CH₃OH
m. pyridine, ClCOCOCl, CH₂Cl₂
n. AlCl₃ benzene/CH₂Cl₂
o. NaBH₄, CH₃OH
p. i-PrOH, HCl/H₂O
q. NaCO₃, NaHCO₃, C₂H₅OH
r. Al₂O₃, HCl/C₂H₅OH R-2-amino-propionic acid, used as a starting material, is first reacted with trifluoroacetyl group to protect the amino group, then reacted with oxalic acid to prepare the corresponding acyl chloride. The acyl chloride is subjected to Friedel-Crafts acylation reaction with benzene in the presence of aluminium chloride, reduction with aluminium isopropoxide, deprotection, and cyclization with aryl nitrogen mustard. Subsequent purification by neutral alumina chromatography gives the target compound (III).

By the method of synthetic route three, the target compounds III-1 and III-2 can be obtained.

Synthetic Route Four:

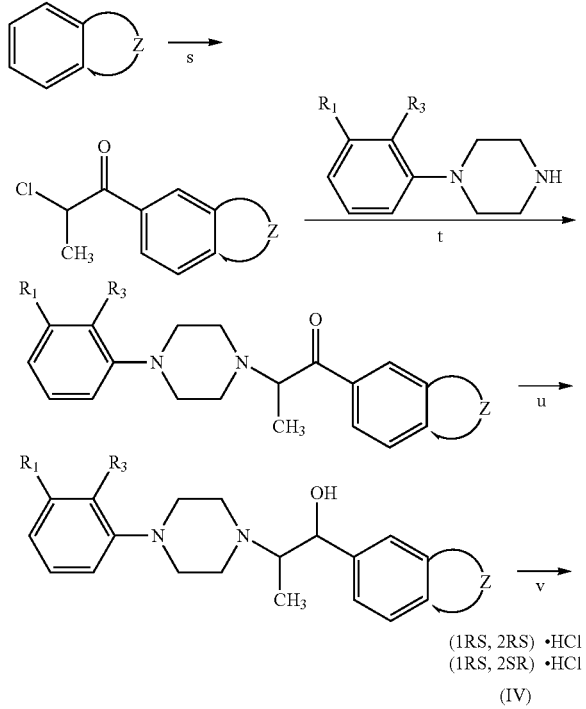

s. 2-chloropropanoyl chloride, AlCl₃, CS₂
t. K₂CO₃, KI, CH₃COCH₃
u. Al(i-PrOH)₃, i-PrOH
v. 1) Al₂O₃ column chromatography,
   2) HCl/C₂H₅OH
R₁: H, CF₃
R₃: H, OCH₃

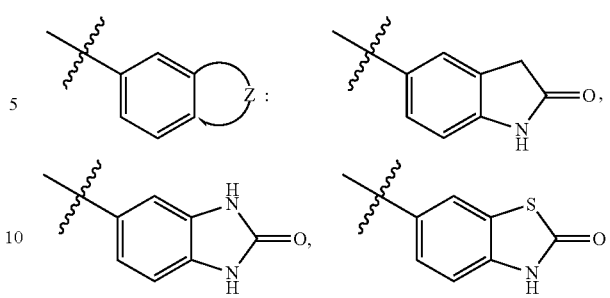

A benzo-heterocyclic compound, used as a starting material, is subjected to Friedel-Crafts acylation reaction with 2-chloropropionyl chloride in the presence of AlCl₃, to obtain the corresponding chloroaryl alkanone, which undergoes condensation with substituted phenylpiperazine. Subsequent reduction gives the target compound (IV).

By the method of synthetic route four, the target compounds IV-1 to IV-6 can be obtained.

General Guideline of Synthetic Route Four (Hereinafter Abbreviated as General Procedure B):

Preparation of (1RS,2SR) and (1RS,2RS)-(1-hydroxy-2-(4-(3-substituted phenyl)piperazinyl)propyl) benzo heterocyclic ketones (IV) hydrochloride 1) preparation of 2-chloroalkyl acyl benzo-heterocyclic ketone At a controlled temperature of 0, a benzo heterocyclic ketone (30 mmol), and AlCl3 (27 g, 0.20 mol) are added to 30 ml of carbon disulfide, and stirred for 20 minutes. The temperature is maintained at 0, and with intense stirring, 2-chloropropionyl chloride (45 mmol) is added dropwise. Stirring is continuously conducted to allow the reaction to proceed for 10 minutes, then the temperature is slowly raised to 50, and the reaction is allowed to proceed for a further 2 hours. The reaction mixture is poured into 150 ml of ice water mixture, and extracted with dichloromethane (3×50 ml). The organic phases are combined, washed with 50 ml saturated brine, dried with anhydrous sodium sulfate, and evaporated till dry under reduced pressure to remove solvent. The resulting solid precipitate is washed with a small amount of ethyl acetate, filtered, and dried, to produce the corresponding 2-chloroalkyl acyl benzo-heterocyclic ketone. The yield is 90 to 95%.

2) Preparation of (1RS,2SR) and (1RS,2RS)-(1-oxy-2-(4-(3-substituted phenyl)piperazinyl)propyl)benzo-heterocyclic ketones The substituted phenyl piperazine (0.01 mol) and 2-chloroalkyl acyl benzo-heterocyclic ketone (0.011 mol) are added to 100 ml of acetonitrile, and stirred at room temperature for 10 minutes. Triethylamine (0.03 mol) is added, and a reaction under refluxing is allowed to proceed at an elevated temperature for 3 hours. The reaction solution is cooled, evaporated till dry to remove solvent, added to 200 ml of chloroform, washed with water (1×50 ml) and saturated brine (1×50 ml), dried with anhydrous sodium sulfate, filtered, and evaporated till dry to remove the solvent. The resulting solid is washed with a small amount of ethyl acetate, filtered and dried, to produce a (1RS,2SR)((1RS,2RS))-(1-oxy-2-(4-(3-substituted phenyl)piperazinyl)propyl)benzo-heterocyclic ketone. The yield is 85 to 90%.

3) Preparation of (1RS,2SR) and (1RS,2RS)-(1-hydroxy-2-(4-(3-substituted phenyl)piperazinyl)propyl) benzo-heterocyclic ketone (IV) hydrochloride The (1RS,2SR)((1RS,2RS))-(1-hydroxy-2-(4-(3-substituted phenyl)piperazinyl)propyl)benzo-heterocyclic ketone (4.0 mmol) is dissolved in 50 ml of methanol solution, and sodium borohydride (8.4 mmol) is added in proportions, mixed, and stirred at room temperature till completion of the reaction. The reaction mixture is cooled with ice water, adjusted to pH of 4 by dropwise addition of 3N hydrochloric acid at a controlled temperature of <20, and stirred for 0.5 hours and then neutralized with saturated sodium bicarbonate solution. 10 ml of water is added, and methanol is removed by rotary evaporation. The mixture is adjusted to pH of 10 with 10% (w/w) NaOH solution, and extracted with chloroform (3×50 ml). The organic phases are combined, washed with 20 ml of saturated brine, dried with anhydrous magnesium sulfate, filtered, and evaporated till dry to remove solvent, to obtain oily product. The oily product is purified by column chromatography (neutral $Al_2O_3$), and eluted with dichloromethane, to obtain threoisomer and erythroisomer. The obtained threoisomer and erythroisomer are separately dissolved in an appropriate amount of ethanol, and adjusted to pH of 2 with $HCl/C_2H_5OH$ (5N). The resulting solid precipitate is filtered, and recrystallized with ethanol or ethanol/water, to respectively obtain (1RS,2SR)-(1-hydroxy-2-(4-(3-substituted phenyl)piperazinyl)propyl)benzo-heterocyclic ketone (IV) hydrochloride, with a yield of 25 to 35%; and (1RS,2RS)-(1-hydroxy-2-(4-(3-substituted phenyl)piperazinyl)propyl)benzo-heterocyclic ketone (IV) hydrochloride, with a yield of 25 to 35%.

On a mice pharmacological model of chemically induced pain, the substituted phenylpiperazine aryl alkanol derivative of the invention shows a relatively strong anti-pain writhing effect and therefore has analgesic activity. Hot plate pharmacological model test in mice also shows that these compounds have analgesic effect.

The results of animal model study show that the compound I-20 has an obvious analgesic effect, and good absorption with oral administration. No drug resistance is observed after multiple applications of the compound I-20. There is a low potential for drug dependence, Ames test exhibits a negative result, and therapeutic index was relative high. Thus, the compound I-20 has the potential to be developed into a new non-narcotic analgesic.

In addition, the substituted phenylpiperazine aryl alkanol derivative of the invention has relatively low toxicity, and small neurological side effect.

Therefore, one embodiment of the invention comprises the use of the substituted phenylpiperazine aryl alkanol derivative in preparing analgesic drugs.

The substituted phenylpiperazine aryl alkanol derivative of the invention can also be used for the preparation of other drugs for central nervous system disorders, for example, drugs for the treatment of neuropathic pain, mania, anxiety disorders, various kinds of depression, schizophrenia, Parkinson's disease (PD), Huntington's disease (HD), Alzheimer's disease, senile dementia, Alzheimer's type dementia, memory disorders, loss of executive function, vascular dementia and other dementias, as well as intellectual, learning or memory dysfunction.

The derivative of the present invention can be administrated in the form of a composition, orally or by injection. Typical daily dosage is 0.1 to 3 mg/kg (orally) or 0.02 to 2 mg/kg (by injection), and can be adjusted by a physician according to the results of clinical trials and patient's condition, age and other factors.

The composition comprises a therapeutically effective amount of the derivative of the invention, and a pharmaceutically acceptable carrier.

The carrier can be any carrier commonly used in pharmaceutical field, for example, diluent, excipient such as water; adhesives such as cellulose derivative, gelatin, polyvinylpyrrolidone; filler such as starch; cracking agent such as calcium carbonate, sodium bicarbonate; lubricant such as calcium stearate or magnesium stearate. Other auxiliary agents such as flavor and sweetener can also be added to the composition. When used for oral administration, it may be prepared in a conventional solid preparation form such as tablet, powder or capsules; and when used for injection, it can be prepared in an injection solution form.

Various formulations of the composition of the invention can be prepared by conventional methods in medical field, in which the content of the active ingredient is 0.1% to 99.5% by weight.

The substituted phenylpiperazine aryl alkanol derivative of the invention and its physiological acceptable salt have analgesic effect on various types of pain, including nociceptive pain, acute pain, chronic pain, neuropathic pain, psychoalgalia and mixed pain. In particular, the pain includes, but is not limited to, post-operative pain, neurogenic pain, central pain, body pain, visceral pain, chronic back pain, neck and waist pain, cancer pain, inflammatory pain, diabetic neuropathic pain, sciatica, tension headache, cluster headache, chronic daily headache, herpes neuralgia, facial and mouth neuralgia, and myofascial pain syndrome, pseudo-limb pain, residual limb pain and paraplegia pain, tooth pain, opioid resistant pain, including postoperative pain after heart surgery and breast surgery, angina, pelvic pain, and urogenital tract pains including cystitis and vaginal vestibulitis and testicular pain, and premenstrual pain syndrome, post stroke pain, irritable bowel syndrome, fatigue and labor pain, pain after childbirth, pain resulting from burns and chemical damage or sun burn, and bone-injury pain.

The substituted phenylpiperazine aryl alkanol derivative of the invention and its physiologically acceptable salt have useful pharmaceutical properties and good tolerability, particularly when applied as new analgesic drugs. These compounds are non-addictive central analgesic agents, show no sedation effect in animal test, and have minimal side effects and relatively high safety index.

The invention will be described in more detail with reference to the following examples. It should be understood that these examples are only provided for purpose of illustration, and are not to be construed as limiting the invention in any way.

Example 1

Preparation of (1RS,2SR)-1-phenyl-2-(4-(3-trifluoromethylphenyl)piperazinyl)-propan-1-ol (I-1) hydrochloride and (1RS,2RS)-1-phenyl-2-(4-(3-trifluoromethylphenyl)piperazinyl)-propan-1-ol (I-2) hydrochloride 2-bromo-1-phenylpropan-1-one was prepared from propiophenone according to the synthetic and working-up method of general procedure A. 2-bromo-1-phenylpropan-1-one (2.56 g, 0.012 mol) and 3-trifluoromethylphenyl piperazine (2.30 g, 0.01 mol) were dissolved in 50 ml acetone, and anhydrous potassium carbonate (4.15 g, 0.03 mol) and potassium iodide (0.17 g, 1 mmol) were added. A reaction under refluxing was allowed to proceed at an elevated temperature for 5 hours. Working up according to general procedure A gave 3.30 g of 1-phenyl-2-(4-(3-trifluoromethylphenyl)piperazinyl)propan-1-one hydrochloride. The yield was 82.5%.

The 1-phenyl-2-(4-(3-trifluoromethylphenyl)piperazinyl)propan-1-one hydrochloride (1.60 g, 4 mmol) was dissolved in 30 ml methanol, and sodium borohydride (0.15 g, 8.4 mmol) was added in proportions, mixed, and stirred at room temperature for 3 hours. Working up according to general procedure A gave 0.54 g of (1RS,2SR)-1-phenyl-2-(4-(3-trifluoromethylphenyl)piperazinyl)propan-1-ol (I-1) hydrochloride having a melting point of 214 to 216° C., with a yield of 33.8%, and 0.49 g of (1RS,2RS)-1-phenyl-2-(4-(3-trifluoromethylphenyl)piperazinyl)propan-1-ol hydrochloride having a melting point of 248 to 250° C., with a yield of 30.6%.

(1RS,2SR)-1-phenyl-2-(4-(3-trifluoromethylphenyl)piperazinyl)propan-1-ol hydrochloride Elemental analysis: $C_{20}H_{23}F_3N_2O \cdot HCl \cdot H_2O$ (theoretical value %: C, 57.35; H, 6.26; N, 6.69; Cl, 8.46; experimental values % C, 57.31; H, 6.24; N, 6.70; Cl, 8.47); MS: m/z 364.18 ($M^+$)

$^1$HNMR (DMSO-$d_6$): δ0.99 (d, 3H), 3.22-3.99 (m, 8H, A-H), 4.03-4.07 (m, 1H, NCH), 4.73 (d, 1H, J=10.0 Hz, CHOH), 7.14-7.17 (d, 1H, Ar—H), 7.27-7.50 (m, 8H, Ar—H), 9.71 (br, 1H, HCl)

(1RS,2RS)-1-phenyl-2-(4-(3-trifluoromethylphenyl)piperazinyl)propan-1-ol hydrochloride Elemental analysis: $C_{20}H_{23}F_3N_2O \cdot HCl \cdot H_2O$ (theoretical value %: C, 57.35; H, 6.26; N, 6.69; Cl, 8.46; experimental values % C, 57.38; H, 6.27; N, 6.71; Cl, 8.48); MS: m/z 364.18 ($M^+$)

$^1$HNMR (DMSO-$d_6$): δ1.06 (d, 3H), 3.30-4.02 (m, 8H, A-H), 5.55 (m, 1H, NCH), 6.14 (s, 1H, CHOH), 7.15-7.47 (m, 8H, Ar—H), 10.95 (br, 1H, HCl).

Example 2

Preparation of (1RS,2SR)-1-phenyl-2-(4-(3-chlorophenyl)piperazinyl)propan-1-ol (I-3) hydrochloride and (1RS,2RS)-1-phenyl-2-(4-(3-chlorophenyl)piperazinyl)propan-1-ol (I-4) hydrochloride 2-bromo-1-phenylpropan-1-one (2.56 g, 0.012 mol) and 3-chlorophenyl piperazine (1.97 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.07 g of 1-phenyl-2-(4-(3-chlorophenyl)piperazinyl)propan-1-one hydrochloride. The yield was 84.0%.

1-phenyl-2-(4-(3-chlorophenyl)piperazinyl)propan-1-one hydrochloride (1.46 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.45 g of (1RS,2SR)-1-phenyl-2-(4-(3-chlorophenyl)piperazinyl)propan-1-ol (I-3) hydrochloride having a melting point of 197 to 199° C., with a yield of 30.6%; and 0.47 g of (1RS,2RS)-1-phenyl-2-(4-(3-chlorophenyl)piperazinyl)propan-1-ol (I-4) hydrochloride having a melting point of 236 to 238° C., with a yield of 32.0%.

(1RS,2SR)-1-phenyl-2-(4-(3-chlorophenyl)piperazinyl)propan-1-ol hydrochloride $^1$HNMR (DMSO-$d_6$): δ0.99 (d, 3H, J=6.8 Hz), 3.19-3.99 (m, 8H, A-H), 4.74 (d, 1H, J=10.0 Hz, CHOH), 5.03 (br, 1H, NCH), 6.86 (d, 1H, J=8.0 Hz), 6.97 (d, 1H, J=8.0 Hz), 7.06 (s, 1H), 7.26 (t, 1H, J=8.0 Hz), 7.33-7.44 (m, 5H, Ar—H), 9.89 (br, 1H, HCl)
MS: m/z 330.15 ($M^+$)

(1RS,2RS)-1-phenyl-2-(4-(3-chlorophenyl)piperazinyl)propan-1-ol hydrochloride $^1$HNMR (DMSO-$d_6$): δ1.04 (d, 3H, J=6.8 Hz), 3.26-3.98 (m, 8H, A-H), 5.50 (br, 1H, NCH), 6.13 (d, 1H, J=4.0 Hz, CHOH), 6.87 (d, 1H, J=8.0 Hz), 6.99 (d, 1H, J=8.0 Hz), 7.07 (s, 1H), 7.27 (t, 1H, J=8.0 Hz), 7.29-7.46 (m, 5H, Ar—H), 10.68 (br, 1H, HCl)
MS: m/z 330.15 ($M^+$).

Example 3

Preparation of (1RS,2SR)-1-phenyl-2-(4-(2,3-dimethylphenyl)piperazinyl)propan-1-ol (I-5) hydrochloride and (1RS,2RS)-1-phenyl-2-(4-(2,3-dimethylphenyl)piperazinyl)propan-1-ol (I-6) hydrochloride 2-bromo-1-phenylpropan-1-one (2.56 g, 0.012 mol) and 2,3-dimethylphenyl piperazine (1.90 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.12 g of 1-phenyl-2-(4-(2,3-dimethylphenyl)piperazinyl)propan-1-one hydrochloride. The yield was 86.9%.

The 1-phenyl-2-(4-(2,3-dimethylphenyl)piperazinyl)propan-1-one hydrochloride (1.44 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.44 g of (1RS,2SR)-1-phenyl-2-(4-(2,3-dimethylphenyl)piperazinyl)propan-1-ol (I-5) hydrochloride having a melting point of 237 to 239° C., with a yield of 30.5%; and 0.39 g of (1RS,2RS)-1-phenyl-2-(4-(2,3-dimethylphenyl)piperazinyl)propan-1-ol (I-6) hydrochloride having a melting point of 259° C. (dec.), with a yield of 27.1%.

(1RS,2SR)-1-phenyl-2-(4-(2,3-dimethylphenyl)piperazinyl)propan-1-ol hydrochloride $^1$HNMR (DMSO-$d_6$): δ1.04 (d, 3H), 2.18 (s, 3H), 2.22 (s, 3H), 3.09-3.57 (m, 8H, A-H), 3.62-3.67 (m, 1H, NCH), 4.73 (d, 1H, J=10.0 Hz, CHOH), 6.91-6.95 (dd, 2H, J=7.6 Hz, J=3.2 Hz), 7.08 (t, 1H, J=7.6 Hz), 7.34-7.45 (m, 5H, Ar—H), 9.66 (br, 1H, HCl)
MS: m/z 324.2 ($M^+$);

(1RS,2RS)-1-phenyl-2-(4-(2,3-dimethylphenyl)piperazinyl)propan-1-ol hydrochloride $^1$HNMR (DMSO-$d_6$): δ1.08 (d, 3H), 2.19 (s, 3H), 2.23 (s, 3H), 3.18-3.77 (m, 8H, A-H), 5.52-5.54 (m, 1H, NCH), 6.11-6.13 (m, 1H, CHOH), 6.94-7.46 (m, 8H, Ar—H), 10.49 (br, 1H, HCl)
MS: m/z 324.2 ($M^+$).

Example 4

Preparation of (1RS,2SR)-1-phenyl-2-(4-(4-methoxyphenyl)piperazinyl)propan-1-ol (I-7) hydrochloride and (1RS,2RS)-1-phenyl-2-(4-(4-methoxyphenyl)piperazinyl)propan-1-ol (I-8) hydrochloride 2-bromo-1-phenylpropan-1-one (2.56 g, 0.012 mol) and 4-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.05 g of 1-phenyl-2-(4-(4-methoxyphenyl)piperazinyl)propan-1-one hydrochloride. The yield was 84.5%.

The 1-phenyl-2-(4-(4-methoxyphenyl)piperazinyl)propan-1-one hydrochloride (1.44 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.46 g of (1RS,2SR)-1-phenyl-2-(4-(4-methoxyphenyl)piperazinyl)propan-1-ol (I-7) hydrochloride having a melting point of 221 to 223° C., with a yield of 31.7%; and 0.44 g of (1RS,2RS)-1-phenyl-2-(4-(4-methoxyphenyl)piperazinyl)propan-1-ol (I-8) hydrochloride having a melting point of 246 to 248° C., with a yield of 30.3%.

(1RS,2SR)-1-phenyl-2-(4-(4-methoxyphenyl)piperazinyl)propan-1-ol hydrochloride $^1$HNMR (DMSO-$d_6$): δ1.00 (d, 3H, J=6.8 Hz), 3.16-3.60 (m, 6H, A-H), 3.62-3.74 (m, 3H, A-H, NCH), 3.70 (s, 3H, OCH3), 4.73 (d, 1H, J=10.0 Hz, CHOH), 6.88 (d, 2H, J=8.8 Hz), 7.03 (d, 2H, J=8.8 Hz), 7.33-7.45 (m, 5H, Ar—H), 9.80 (br, 1H, HCl)

MS: m/z 326.2 (M$^+$)

(1RS,2RS)-1-phenyl-2-(4-(4-methoxyphenyl)piperazinyl)propan-1-ol hydrochloride $^1$HNMR (DMSO-$d_6$): δ1.05 (d, 3H, J=6.8 Hz), 3.30-3.83 (m, 9H, A-H, NCH), 3.71 (s, 3H, OCH3), 5.56 (s, 1H, CHOH), 6.89 (d, 2H, J=8.8 Hz), 7.05 (d, 2H, J=8.8 Hz), 7.28 (t, 1H, J=7.2 Hz), 7.38 (t, 2H, J=7.2 Hz), 7.45 (d, 2H, J=7.2 Hz), 11.03 (br, 1H, HCl)

MS: m/z 326.2 (M$^+$)

Example 5

Preparation of (1RS,2SR)-1-phenyl-2-(4-(3-methoxyphenyl)piperazinyl)propan-1-ol (I-9) hydrochloride and (1RS,2RS)-1-phenyl-2-(4-(3-methoxyphenyl)piperazinyl)propan-1-ol (I-10) hydrochloride 2-bromo-1-phenylpropan-1-one (2.56 g, 0.012 mol) and 3-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 2.97 g of 1-phenyl-2-(4-(3-methoxy-phenyl)piperazinyl)propan-1-one hydrochloride. The yield was 82.3%.

The 1-phenyl-2-(4-(3-methoxy-phenyl)piperazinyl)propan-1-one hydrochloride (1.44 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.40 g of (1RS,2SR)-1-phenyl-2-(4-(3-methoxyphenyl)piperazinyl)propan-1-ol (I-9) hydrochloride having a melting point of 214 to 216° C., with a yield of 27.6%; and 0.38 g of (1RS,2RS)-1-phenyl-2-(4-(3-methoxyphenyl)piperazinyl)propan-1-ol (I-10) hydrochloride having a melting point of 225 to 227° C., with a yield of 26.2%.

(1RS,2SR)-1-phenyl-2-(4-(3-methoxyphenyl)piperazinyl)propan-1-ol hydrochloride $^1$HNMR (DMSO-$d_6$): δ0.99 (d, 3H, J=7.2 Hz), 3.13-3.57 (m, 6H, A-H), 3.63-3.68 (m, 1H, J=7.2 Hz, NCH), 3.72 (s, 3H, OCH3), 3.82-4.02 (m, 2H, A-H), 4.73 (d, 1H, J=10.0 Hz, CHOH), 6.48 (dd, 1H, J=8.8 Hz, J=2.0 Hz), 6.53 (t, 1H, J=2.0 Hz), 6.59 (dd, 1H, J=8.8 Hz, J=2.0 Hz), 7.16 (d, 1H, J=8.8 Hz), 7.33-7.45 (m, 5H, Ar—H), 9.76 (br, 1H, HCl)

MS: m/z 326.2 (M$^+$).

(1RS,2RS)-1-phenyl-2-(4-(3-methoxyphenyl)piperazinyl)propan-1-ol hydrochloride $^1$HNMR (DMSO-$d_6$): δ1.05 (d, 3H, J=6.8 Hz), 3.20-3.41 (m, 4H, A-H), 3.54-3.57 (m, 1H, NCH), 3.63-3.90 (m, 4H, A-H), 3.73 (s, 3H, OCH3), 5.54 (s, 1H, CHOH), 6.45 (dd, 1H, J=8.0 Hz, J=2.0 Hz), 6.54 (t, 1H, J=2.0 Hz), 6.59 (dd, 1H, J=8.0 Hz, J=2.0 Hz), 7.16 (d, 1H, J=8.0 Hz), 7.28 (t, 1H, J=7.2 Hz), 7.38 (t, 2H, J=7.2 Hz), 7.45 (d, 2H, J=7.2 Hz), 10.83 (br, 1H, HCl)

MS: m/z 326.2 (M$^+$).

Example 6

Preparation of (1RS,2SR)-1-(4-fluorophenyl)-2-(4-(2-methoxyphenyl)piperazinyl)propan-1-ol (I-11) hydrochloride and (1RS,2RS)-1-(4-fluorophenyl)-2-(4-(2-methoxyphenyl)piperazinyl)propan-1-ol (I-12) hydrochloride 2-bromo-1-(4-fluorophenyl)propan-1-one was prepared from 1-(4-fluorophenyl)propan-1-one according to the synthetic and working-up method of general procedure A. 2-bromo-1-(4-fluorophenyl)propan-1-one (2.77 g, 0.012 mol) and 3-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.06 g of 1-(4-fluorophenyl)-2-(4-(3-methoxyphenyl)piperazinyl)propan-1-one hydrochloride. The yield was 80.8%.

The 1-(4-fluorophenyl)-2-(4-(3-methoxyphenyl)piperazinyl)propan-1-one hydrochloride (1.52 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.43 g of (1RS,2SR)-1-(4-fluorophenyl)-2-(4-(3-methoxyphenyl)piperazinyl)propan-1-ol (I-11) hydrochloride having a melting point of 203 to 205° C., with a yield of 28.3%; and 0.39 g of (1RS,2RS)-1-(4-fluorophenyl)-2-(4-(3-methoxyphenyl)piperazinyl)propan-1-ol (I-12) hydrochloride having a melting point of 232 to 234° C., with a yield of 25.7%.

(1RS,2SR)-1-(4-fluorophenyl)-2-(4-(2-methoxyphenyl)piperazinyl)propan-1-ol hydrochloride $^1$HNMR (DMSO-d$_6$): δ1.02 (d, 3H, J=6.8 Hz), 3.09-3.63 (m, 9H, A-H, NCH), 3.75 (s, 3H, OCH3), 3.80 (s, 3H, OCH3), 4.69 (d, 1H, J=10.0 Hz, CHOH), 6.78-7.45 (m, 8H, Ar—H), 9.87 (br, 1H, HCl)
MS: m/z 344.2 (M$^+$).

(1RS,2RS)-1-(4-fluorophenyl)-2-(4-(2-methoxyphenyl)piperazinyl)propan-1-ol hydrochloride $^1$HNMR (DMSO-d$_6$): δ1.07 (d, 3H, J=6.8 Hz), 3.12-3.68 (m, 8H, A-H), 3.75 (s, 3H, OCH3), 3.80 (s, 3H, OCH3), 4.66-4.68 (m, 1H, NCH), 5.50 (br, 1H, CHOH), 6.78-7.47 (m, 8H, Ar—H), 10.79 (br, 1H, HCl)
MS: m/z 344.2 (M$^+$).

Example 7

Preparation of (1RS,2SR)-1-(4-methoxyphenyl)-2-(4-(2-methoxyphenyl)piperazinyl)propan-1-ol (I-13) hydrochloride and (1RS,2RS)-1-(4-methoxyphenyl)-2-(4-(2-methoxyphenyl)piperazinyl)propan-1-ol (I-14) hydrochloride 2-bromo-1-(4-methoxyphenyl)propan-1-one was prepared from 1-(4-methoxyphenyl)propan-1-one according to the synthetic and working-up method of general procedure A. 2-bromo-1-(4-methoxyphenyl)propan-1-one (2.77 g, 0.012 mol) and 2-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.26 g of 1-(4-methoxyphenyl)-2-(4-(2-methoxyphenyl)piperazinyl)propan-1-one hydrochloride. The yield was 83.4%.

The 1-(4-methoxyphenyl)-2-(4-(2-methoxyphenyl)piperazinyl)propan-1-one hydrochloride (1.56 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.49 g of (1RS, 2SR)-1-(4-methoxyphenyl)-2-(4-(2-methoxyphenyl)piperazinyl)propan-1-ol (I-13) hydrochloride having a melting point of 199 to 201° C., with a yield of 31.2%; and 0.44 g of (1RS, 2RS)-1-(4-methoxyphenyl)-2-(4-(2-methoxyphenyl)piperazinyl)propan-1-ol (I-14) hydrochloride having a melting point of 224 to 226° C., with a yield of 28%.

(1RS,2SR)-1-(4-methoxyphenyl)-2-(4-(2-methoxyphenyl)piperazinyl)propan-1-ol hydrochloride $^1$HNMR (DMSO-d$_6$): δ1.01 (d, 3H, J=6.8 Hz), 3.11-3.61 (m, 9H, A-H, NCH), 3.76 (s, 3H, OCH3), 3.80 (s, 3H, OCH3), 4.67 (d, 1H, J=10.0 Hz, CHOH), 6.89-7.05 (m, 6H, Ar—H), 7.33 (d, 2H, J=8.4 Hz), 9.69 (br, 1H, HCl)
MS: m/z 356.2 (M$^+$);

(1RS,2RS)-1-(4-methoxyphenyl)-2-(4-(2-methoxyphenyl)piperazinyl)propan-1-ol hydrochloride $^1$HNMR (DMSO-d$_6$): δ1.06 (d, 3H, J=6.8 Hz), 3.10-3.66 (m, 8H, A-H), 3.74 (s, 3H, OCH3), 3.80 (s, 3H, OCH3), 4.66 (m, 1H, NCH), 5.49 (s, 1H, CHOH), 6.89-7.05 (m, 6H, Ar—H), 7.32-7.37 (m, 2H, Ar—H), 10.74 (br, 1H, HCl)
MS: m/z 356.2 (M$^+$).

Example 8

Preparation of (1RS,2SR)-1-(4-acetylamino-phenyl)-2-(4-(3-trifluoromethylphenyl)piperazinyl)propan-1-ol (I-15) hydrochloride and (1RS,2RS)-1-(4-acetylamino-phenyl)-2-(4-(3-trifluoromethylphenyl)piperazinyl)propan-1-ol (I-16) hydrochloride N-(4-(2-bromopropanoyl)phenyl)acetamide was prepared from N-(4-propionylphenyl)acetamide according to the synthetic and working-up method of general procedure A. N-(4-(2-bromopropanoyl)phenyl)acetamide (3.24 g, 0.012 mol) and 3-trifluoromethylphenyl piperazine (2.30 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.88 g of 1-(4-acetylaminophenyl)-2-(4-(3-trifluoromethylphenyl)piperazinyl)propan-1-one hydrochloride. The yield was 85.1%.

The 1-(4-acetylaminophenyl)-2-(4-(3-trifluoromethylphenyl)piperazinyl)propan-1-one hydrochloride (1.82 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.54 g of (1RS, 2SR)-1-(4-acetylaminophenyl)-2-(4-(3-trifluoromethylphenyl)piperazinyl)propan-1-ol (I-15) hydrochloride having a melting point of 211 to 213° C., with a yield of 29.5%; and 0.51 g of (1RS,2RS)-1-(4-acetylaminophenyl)-2-(4-(3-trifluoromethylphenyl)piperazinyl)propan-1-ol (I-16) hydrochloride having a melting point of 245 to 247° C., with a yield of 27.9%.

(1RS,2SR)-1-(4-acetylaminophenyl)-2-(4-(3-trifluoromethylphenyl)piperazinyl)propan-1-ol hydrochloride $^1$HNMR (DMSO-d$_6$): δ0.97 (d, 3H), 2.35 (s, 3H), 3.20-4.01 (m, 8H, A-H), 4.03-4.10 (m, 1H), 4.75 (d, 1H, J=10.0 Hz), 6.80-7.98 (m, 8H, Ar—H), 9.89 (br, 1H, HCl), 10.12 (s, 1H)
MS: m/z 421.2 (M$^+$);

(1RS,2RS)-1-(4-acetylaminophenyl)-2-(4-(3-trifluoromethylphenyl)piperazinyl)propan-1-ol hydrochloride $^1$HNMR (DMSO-d$_6$): δ1.06 (d, 3H), 2.37 (s, 3H), 3.22-4.04 (m, 8H, A-H), 4.05-4.15 (m, 1H), 6.21 (s, 1H, CHOH), 6.77-8.01 (m, 8H, Ar—H), 9.92 (br, 1H, HCl), 10.53 (s, 1H)
MS: m/z 421.2 (M$^+$).

Example 9

Preparation of (1RS,2SR)-1-(4-methanesulfonamido phenyl)-2-(4-(3-trifluoromethylphenyl)piperazinyl)propan-1-ol (I-17) hydrochloride and (1RS,2RS)-1-(4-methanesulfonamido phenyl)-2-(4-(3-trifluoromethylphenyl)piperazinyl)propan-1-ol (I-18) hydrochloride N-(4-(2-bromopropanoyl)phenyl)methanesulfonamide was prepared from N-(4-propionylphenyl)methanesulfonamide according to the synthetic and working-up method of general procedure A. N-(4-(2-bromopropanoyl)phenyl)methanesulfonamide (3.67 g, 0.012 mol) and 3-trifluoromethylphenyl piperazine (2.30 g, 0.01 mol) were dissolved in 50 ml of acetone, and anhydrous carbonate potassium (4.15 g, 0.03 mol) and potassium iodide (0.17 g, 1 mmol) were added. A reaction under refluxing was allowed to proceed for 5 hours at an elevated temperature. Working up according to general procedure A gave 4.02 g of 1-(4-methanesulfonamido phenyl)-2-(4-(3-trifluoromethylphenyl)piperazinyl)propan-1-one hydrochloride. The yield was 81.7%.

The 1-(4-methanesulfonamido phenyl)-2-(4-(3-trifluoromethylphenyl)piperazinyl)propan-1-one hydrochloride (1.97 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.60 g of (1RS, 2SR)-1-(4-methanesulfonamido phenyl)-2-(4-(3-trifluoromethylphenyl)piperazinyl)propan-1-ol (I-17) hydrochloride having a melting point of 222 to 224° C., with a yield of 31.4%; and 0.55 g of (1RS,2RS)-1-(4-methanesulfonamido phenyl)-2-(4-(3-trifluoromethylphenyl)piperazinyl)propan-1-ol (I-18) hydrochloride having a melting point of 243 to 245° C., with a yield of 28.8%.

(1RS,2SR)-1-(4-methanesulfonamido phenyl)-2-(4-(3-trifluoromethylphenyl)piperazinyl)propan-1-ol hydrochloride $^1$HNMR (DMSO-d$_6$): δ0.99 (d, 3H), 2.82 (s, 3H), 3.21-3.99 (m, 8H, A-H), 4.03-4.62 (m, 2H), 4.74 (d, 1H, J=10.0 Hz), 6.43-7.98 (m, 8H, Ar—H), 9.93 (br, 1H, HCl)
MS: m/z 457.2 (M$^+$)

(1RS,2RS)-1-(4-methanesulfonamido phenyl)-2-(4-(3-trifluoromethylphenyl)piperazinyl)propan-1-ol hydrochloride $^1$HNMR (DMSO-d$_6$): δ1.07 (d, 3H), 2.83 (s, 3H), 3.18-4.01 (m, 8H, A-H), 4.04-4.76 (m, 2H), 6.17 (s, 1H), 6.49-8.12 (m, 8H, Ar—H), 10.43 (br, 1H, HCl)
MS: m/z 457.2 (M$^+$).

Example 10

Preparation of (1RS,2SR)-1-phenyl-2-(4-(2-methoxyphenyl)piperazinyl)propan-1-ol (I-19) hydrochloride and (1RS,2RS)-1-phenyl-2-(4-(2-methoxyphenyl)piperazinyl)propan-1-ol (I-20) hydrochloride 2-bromo-1-phenylpropan-1-one was prepared from propiophenone according to the synthetic and working-up method of general procedure A. 2-bromo-1-phenylpropan-1-one (2.56 g, 0.012 mol) and 2-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.13 g of 1-phenyl-2-(4-(2-methoxyphenyl)piperazinyl)propan-1-one hydrochloride. The yield was 86.7%.

The 1-phenyl-2-(4-(2-methoxyphenyl)piperazinyl)propan-1-one hydrochloride (1.44 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.49 g of (1RS,2SR)-1-phenyl-2-(4-(2-methoxyphenyl)piperazinyl)propan-1-ol (I-19) hydrochloride having a melting point of 206 to 208° C., with a yield of 33.8%; and 0.42 g of (1RS,2RS)-1-phenyl-2-(4-(2-methoxyphenyl)piperazinyl)propan-1-ol (I-20) hydrochloride having a melting point of 238 to 240° C., with a yield of 28.9%.

(1RS,2SR)-1-phenyl-2-(4-(2-methoxyphenyl)piperazinyl)propan-1-ol hydrochloride $^1$HNMR (DMSO-d$_6$): δ0.97 (m, 3H), 3.35-3.61 (m, 9H), 3.73 (s, 3H, OCH3), 4.64 (d, 1H, J=10.0 Hz, CHOH), 6.90-7.11 (m, 4H, Ar—H), 7.28-7.40 (m, 5H, Ar—H)
MS: m/z 326.2 (M$^+$);

(1RS,2RS)-1-phenyl-2-(4-(2-methoxyphenyl)piperazinyl)propan-1-ol hydrochloride $^1$HNMR (DMSO-d$_6$): δ1.06 (d, 3H, J=6.8 Hz), 3.19-3.76 (m, 9H, A-H), 3.80 (s, 3H, OCH3), 5.56 (s, 1H, CHOH), 6.89-7.06 (m, 4H, Ar—H), 7.25-7.47 (m, 5H, Ar—H), 10.92 (br, 1H, HCl)
MS: m/z 326.2 (M$^+$).

Example 11

Preparation of (1RS,2SR)-1-phenyl-2-(4-(2-methoxyphenyl)piperazinyl)butan-1-ol (I-21) hydrochloride and (1RS,2RS)-1-phenyl-2-(4-(2-methoxyphenyl)piperazinyl)butan-1-ol (I-22) hydrochloride 2-bromo-1-phenylbutan-1-one was prepared from butyrophenone according to the synthetic and working-up method of general procedure A. 2-bromo-1-phenylbutan-1-one (2.27 g, 0.012 mol) and 2-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.21 g of 1-phenyl-2-(4-(2-methoxyphenyl)piperazinyl)butan-1-one hydrochloride. The yield was 85.6%.

The 1-phenyl-2-(4-(2-methoxyphenyl)piperazinyl)butan-1-one hydrochloride (1.50 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.46 g of (1RS,2SR)-1-phenyl-2-(4-(2-methoxyphenyl)piperazinyl)butan-1-ol (I-21) hydrochloride having a melting point of 206 to 208° C., with a yield of 30.5%; and 0.40 g of (1RS,2RS)-1-phenyl-2-(4-(2-methoxyphenyl)piperazinyl)butan-1-ol (I-22) hydrochloride having a melting point of 224 to 226° C., with a yield of 27.2%.

(1RS,2SR)-1-phenyl-2-(4-(2-methoxyphenyl)piperazinyl) butan-1-ol hydrochloride $^1$HNMR (DMSO-d$_6$): δ0.48 (t, 3H, J=7.2 Hz), 1.43-1.51 (m, 1H), 1.78-1.85 (m, 1H), 3.03-3.37 (m, 9H), 3.78 (s, 3H, OCH3), 4.76 (d, 1H, J=9.6 Hz, CHOH), 6.88-7.05 (m, 4H, Ar—H), 7.34-7.50 (m, 5H, Ar—H), 9.51 (br, 1H, HCl)
MS: m/z 340.2 (M$^+$);

(1RS,2RS)-1-phenyl-2-(4-(2-methoxyphenyl)piperazinyl) butan-1-ol hydrochloride $^1$HNMR (DMSO-d$_6$): δ0.51 (t, 3H, J=7.2 Hz), 1.58-1.65 (m, 1H), 1.82-1.91 (m, 1H), 3.16-3.80 (m, 9H), 3.82 (s, 3H, OCH3), 5.52 (s, 1H, CHOH), 6.90-7.06 (m, 4H, Ar—H), 7.26-7.52 (m, 5H, Ar—H), 10.32 (br, 1H, HCl)

MS: m/z 340.2 (M+).

Example 12

Preparation of (1RS,2SR)-1-phenyl-2-(4-(2-methoxyphenyl)piperazinyl)pentan-1-ol (I-23) hydrochloride and (1RS,2RS)-1-phenyl-2-(4-(2-methoxyphenyl)piperazinyl)pentan-1-ol (I-24) hydrochloride 2-bromo-1-phenylpentan-1-one was prepared from 1-phenylpentan-1-one according to the synthetic and working-up method of general procedure A. 2-bromo-1-phenylpentan-1-one (2.41 g, 0.012 mol) and 2-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.20 g of 1-phenyl-2-(4-(2-methoxyphenyl)piperazinyl)pentan-1-one hydrochloride. The yield was 82.3%.

The 1-phenyl-2-(4-(2-methoxyphenyl)piperazinyl)pentan-1-one hydrochloride (1.56 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.47 g of (1RS,2SR)-1-phenyl-2-(4-(2-methoxyphenyl)piperazinyl)pentan-1-ol (I-23) hydrochloride having a melting point of 215 to 217° C., with a yield of 30.1%; and 0.39 g of (1RS,2RS)-1-phenyl-2-(4-(2-methoxyphenyl)piperazinyl)pentan-1-ol (I-24) hydrochloride having a melting point of 222 to 224° C., with a yield of 25.6%.

(1RS,2SR)-1-phenyl-2-(4-(2-methoxyphenyl)piperazinyl)pentan-1-ol hydrochloride $^1$HNMR (DMSO-$d_6$): δ0.57 (t, 3H, J=7.2 Hz), 0.96-1.02 (m, 1H), 1.34-1.40 (m, 1H), 1.66-1.72 (m, 1H), 3.10-3.65 (m, 9H), 3.79 (s, 3H, OCH3), 4.76 (s, 1H, J=10.0 Hz, CHOH), 6.89-7.07 (m, 4H, Ar—H), 7.33-7.50 (m, 5H, Ar—H), 9.75 (br, 1H, HCl)

MS: m/z 354.2 (M+);

(1RS,2RS)-1-phenyl-2-(4-(2-methoxyphenyl)piperazinyl)pentan-1-ol hydrochloride $^1$HNMR (DMSO-$d_6$): δ0.57 (t, 3H, J=7.2 Hz), 0.61-0.69 (m, 1H), 0.94-1.02 (m, 1H), 1.53-1.61 (m, 1H), 1.77-1.86 (m, 1H), 3.25-3.64 (m, 9H), 3.82 (s, 3H, OCH3), 5.58 (s, 1H, CHOH), 6.90-7.07 (m, 4H, Ar—H), 7.26-7.52 (m, 5H, Ar—H), 10.72 (br, 1H, HCl)

MS: m/z 354.2 (M+).

Example 13

Preparation of (1RS,2SR)-1-phenyl-2-(4-(2-methoxyphenyl)piperazinyl)hexan-1-ol (I-25) hydrochloride and (1RS,2RS)-1-phenyl-2-(4-(2-methoxyphenyl)piperazinyl)hexan-1-ol (I-26) hydrochloride 2-bromo-1-phenylhexan-1-one was prepared from hexanophenone according to the synthetic and working-up method of general procedure A. 2-bromo-1-phenylhexan-1-one (3.06 g, 0.012 mol) and 2-methoxyphenyl piperazine (1.92 g, 0.01 mol) were dissolved in 50 ml of acetone, and anhydrous potassium carbonate (4.15 g, 0.03 mol) and potassium iodide (0.17 g, 1 mmol) were added. A reaction under refluxing was allowed to proceed for 5 hours at an elevated temperature. Working up according to general procedure A gave 3.43 g of 1-phenyl-2-(4-(2-methoxyphenyl)piperazinyl)hexan-1-one hydrochloride. The yield was 85.1%.

The 1-phenyl-2-(4-(2-methoxyphenyl)piperazinyl)hexan-1-one hydrochloride (1.61 g, 4 mmol) was dissolved in 30 ml of methanol solution, and sodium borohydride (0.15 g, 8.4 mmol) was added in proportions, mixed, and stirred at room temperature for 3 hours. Working up according to general procedure A gave 0.50 g of (1RS,2SR)-1-phenyl-2-(4-(2-methoxyphenyl)piperazinyl)hexan-1-ol (I-25) hydrochloride having a melting point of 206 to 208° C., with a yield of 30.9%; and 0.44 g of (1RS,2RS)-1-phenyl-2-(4-(2-methoxyphenyl)piperazinyl)hexan-1-ol (I-26) hydrochloride having a melting point of 230 to 232° C., with a yield of 27.2%.

(1RS,2SR)-1-phenyl-2-(4-(2-methoxyphenyl)piperazinyl)hexan-1-ol (I-25) hydrochloride $^1$HNMR (DMSO-$d_6$): δ0.46 (m, 1H), 0.60 (t, 3H, J=7.2 Hz), 0.94-1.05 (m, 3H), 1.38-1.44 (m, 1H), 1.74-1.78 (m, 1H), 3.20-3.63 (m, 9H), 3.81 (s, 3H, OCH3), 4.81 (s, 1H, J=9.6 Hz, CHOH), 6.89-7.06 (m, 4H, Ar—H), 7.34-7.50 (m, 5H, Ar—H), 9.59 (br, 1H, HCl)

MS: m/z 368.3 (M+);

(1RS,2RS)-1-phenyl-2-(4-(2-methoxyphenyl)piperazinyl)hexan-1-ol (I-26) hydrochloride $^1$HNMR (DMSO-$d_6$): δ0.54-0.61 (m, 4H), 0.95-1.03 (m, 3H), 0.94-1.02 (m, 1H), 1.52-1.59 (m, 1H), 1.81-1.86 (m, 1H), 3.20-3.79 (m, 9H), 3.82 (s, 3H, OCH3), 5.55 (s, 1H, CHOH), 6.90-7.07 (m, 4H, Ar—H), 7.26-7.51 (m, 5H, Ar—H), 10.51 (br, 1H, HCl)

MS: m/z 368.3 (M+).

Example 14

Preparation of (1R,2S)-1-phenyl-2-(4-(2-methoxyphenyl)piperazinyl)propan-1-ol (II-1) hydrochloride and (1S,2S)-1-phenyl-2-(4-(2-methoxyphenyl)piperazinyl)propan-1-ol (II-2) hydrochloride 1) Preparation of (S)-2-(1,3-dicarbonyl isoindole) propionic acid (S)-2-amino propionic acid (4.45 g, 0.05 mol), phthalic anhydride (7.40 g, 0.05 mol) and triethylamine (0.8 ml) were added to 150 ml of toluene, and heated till refluxing. A reaction was allowed to proceed for 24 hours. The reaction mixture was cooled, evaporated to remove the solvent, added to 50 ml of water, and extracted with ethyl acetate (3×50 ml). The ethyl acetate layer was washed with saturated brine, dried with anhydrous sodium sulfate, filtered, and evaporated to remove the solvent, thereby obtaining 9.9 g of white solid. The yield was 90.3%.

MS: m/z 219.1.

2) Preparation of (S)-2-(2-(1-carbonyl-1-phenyl) propyl) isoindole-1,3-dione (S)-2-(1,3-dicarbonyl isoindole) propionic acid (5.04 g, 0.023 mol) was dissolved in 40 ml of dichloromethane, and 0.02 g DMF was added dropwise, and stirred for 10 minutes. The mixture was cooled in ice-water bath, and at a controlled temperature of lower than 10, dichloromethane solution of oxalyl chloride (6.35 g, 0.046 mol, 10 ml) was added dropwise. Following the complete of the addition, the temperature was slowly raised to room temperature. A reaction was allowed to proceed for 20 hours. Evaporation was conducted under reduced pressure to remove the solvent, and 2×20 ml of chloroform was added to remove excess oxalyl chloride by azeotropism, obtaining 5.4 g of white solid.

The solid was dissolved in 50 ml of dry dichloromethane, and aluminium chloride (6.14 g, 0.046 mol) was added, and stirred, allowing the reaction to proceed for 10 minutes. The reaction mixture was cooled in ice-water bath, and at a controlled temperature of lower than 10, dichloromethane solution of benzene (2.7 g, 0.035 mol, 30 ml) was added dropwise. Following the complete of the addition, the temperature was slowly raised to room temperature. A reaction was allowed to proceed for 24 hours. The reaction solution was poured into ice water, stirred, and separated. The water phase was extracted with dichloromethane (2×50 ml). The organic phases were combined, washed with saturated brine, dried with anhydrous sodium sulfate, filtered, evaporated to remove the solvent, and recrystallized with ethyl acetate, thereby obtaining 3.5 g of target product. The yield was 54.5%.

3) Preparation of (S)-2-(2-(1-hydroxy-1-phenyl)propyl)isoindole-1,3-dione

Aluminium isopropoxide (0.82 g, 0.004 mol) was dissolved in a mixture of 6.6 g of isopropanol and 10 ml of toluene, and (S)-2-(2-(1-carbonyl-1-phenyl)propyl)isoindole-1,3-dione (2.8 g, 0.01 mol) was added. The temperature was slowly raised to 60, and maintained. A reaction was allowed to proceed for 72 hours. The reaction mixture was cooled, quenched with 50 ml of 1N hydrochloric acid, and separated. The water phase was extracted with 50 ml of ethyl acetate. The organic phases were combined, washed with saturated brine, dried with anhydrous sodium sulfate, filtered, and evaporated to remove the solvent. The residue was purified by neutral alumina chromatography, and eluted with dichloromethane/methanol, obtaining 2.37 g of (S)-2-(2-(1-hydroxy-1-phenyl)propyl)isoindole-1,3-dione. The yield was 84.3%.

4) Preparation of (S)-2-amino-1-phenylpropanol (S)-2-(2-(1-hydroxy-1-phenyl)propyl)isoindole-1,3-dione (5.0 g, 0.018 mol) was dissolved in 40 ml of methanol, and hydrazine hydrate (1.8 g, 0.018 mol) was added. The temperature was slowly raised to 40, and a reaction was allowed to proceed for 0.5 hours. The solvent was removed by evaporation, and 40 ml of ethyl acetate was added, and stirred. Following the separation of phases, the organic phase was washed with saturated brine, dried, and evaporated to remove the solvent, obtaining 2.2 g of (S)-2-amino-1-phenylpropanol. The yield was 80.9%.

5) Preparation of (1R,2S)-1-phenyl-2-(4-(2-methoxyphenyl)piperazinyl)propan-1-ol (II-1) and (1S,2S)-1-phenyl-2-(4-(2-methoxyphenyl)piperazinyl)propan-1-ol (II-2) hydrochloride (S)-2-amino-1-phenylpropanol (0.75 g, 4 mmol), and N,N-bis(2-chloroethyl)-2-methoxyaniline (1.00 g, 4 mmol) were dissolved in 20 ml of ethanol, and sodium bicarbonate (0.68 g, 8 mmol) was added. A reaction under refluxing was allowed to proceed for 12 hours at an elevated temperature. The reaction mixture was cooled, filtered, and evaporated to remove the solvent, giving 1.7 g of oily product, which was purified by neutral alumina chromatography to obtain target compound. The target compound was dissolved in ethanol, and acidified with HCl/$C_2H_5$OH (5N) to form 0.095 g of (1R,2S)-1-phenyl-2-(4-(2-methoxyphenyl)piperazinyl)propan-1-ol (II-1) hydrochlorid salt having a melting point of 210 to 212° C., with a yield of 6.5%; and 0.37 g of (1R,2S)-1-phenyl-2-(4-(2-methoxyphenyl)piperazinyl)propan-1-ol (II-2) hydrochloride having a melting point of 226 to 228° C., with a yield of 25.5%.

(1R,2S)-1-phenyl-2-(4-(2-methoxyphenyl)piperazinyl)propan-1-ol hydrochloride $^1$HNMR (DMSO-$d_6$): δ1.01 (d, 3H, J=6.0 Hz), 3.11-3.63 (m, 9H, AH, NCH), 3.80 (s, 3H, OCH3), 4.73 (d, 1H, J=9.6 Hz, CHOH), 6.91-7.04 (m, 4H, Ar—H), 7.36-7.43 (m, 5H, Ar—H), 9.72 (br, 1H, HCl)
MS: m/z 326.2 (M$^+$)
[α]D20=42.8°

(1S,2S)-1-phenyl-2-(4-(2-methoxyphenyl)piperazinyl)propan-1-ol hydrochloride $^1$HNMR (DMSO-$d_6$): δ1.06 (d, 3H, J=6.8 Hz), 3.20-3.77 (m, 9H, AH, NCH), 3.80 (s, 3H, OCH3), 5.57 (s, 1H, CHOH), 6.89-7.06 (m, 4H, Ar—H), 7.28 (t, 1H, J=7.6 Hz), 7.38 (t, 2H, J=7.6 Hz), 7.46 (m, 2H, J=7.6 Hz), 10.97 (br, 1H, HCl)
MS: m/z 326.2 (M$^+$)
[α]D20=4.5°.

Example 15

Preparation of (1S,2R)-1-phenyl-2-(4-(2-methoxyphenyl)piperazinyl)propan-1-ol (III-1) hydrochloride and (1R,2R)-1-phenyl-2-(4-(2-methoxyphenyl)piperazinyl)propan-1-ol (III-2) hydrochloride 1) Preparation of (R)—N-trifluoroacetyl-2-amino propionic acid (R)-2-amino propionic acid (8.9 g, 0.1 mol) was dissolved in 100 ml of methanol, and 1,1,3,3-tetramethyl guanidine (15.6 g, 0.136 mol) was added. At room temperature, trifluoroethyl acetate (18.5 g, 0.13 mol) was added dropwise. After the completion of the addition, stirring is conducted to allow a reaction to proceed for 5 hours. Most solvent was removed by evaporation, and the residue was poured into 100 ml of water, acidified with 12 ml of concentrated hydrochloric acid, and extracted with ethyl acetate (3×60 ml). The organic phases were combined, washed with saturated brine, dried with anhydrous sodium sulfate, concentrated and crystallized, washed with 160 ml of hexane, filtered, and dried, obtaining 18.0 g of product. The yield was 97.3%. MS: m/z 185.1

2) Preparation of (R)—N-trifluoroacetyl-2-amino propionyl chloride

The compound obtained in step 1) (17.2 g, 0.0845 mol) was dissolved in 300 ml of dichloromethane, and 1 ml of pyridine was added. The reaction mixture was cooled in ice-water bath to 0~3, and oxalyl chloride (25.8 g, 0.203 mol) was added dropwise. After the completion of the addition, the temperature was slowly raised to room temperature, and a reaction was allowed to proceed for 3 hours. Evaporation was carried out under reduced pressure to remove the solvent, and 50 ml×2 benzene was added to remove residual solvent by azeotropism. The obtained (R)—N-trifluoroacetyl-2-amino propionyl chloride can be directly used for the subsequent reaction.

3) Preparation of (R)—N-trifluoroacetyl-2-amino propiophenone (R)—N-trifluoroacetyl-2-amino propionyl chloride prepared as above was dissolved in 40 ml of methylene chloride, and 160 ml of benzene was added. The reaction mixture was cooled in ice-water bath to 0~3, and aluminium chloride (24.7 g, 0.185 mol) was added in proportions. A reaction was allowed to proceed for 2 hours. The temperature was slowly raised to room temperature, and the reaction was allowed to proceed for further 12 hours. The reaction solution was poured into the mixture of 500 ml of ice water and 120 ml of 1N hydrochloric acid, stirred for 10 minutes, and separated. The water phase was extracted with dichloromethane (100 ml×2). The organic phases were combined, washed with saturated brine, dried and concentrated, and purified by neutral alumina chromatography, obtaining 14.72 of pure compound. The yield was 71.0%.

4) Preparation of (R)—N-trifluoroacetyl-2-amino phenyl propanol (R)—N-trifluoroacetyl-2-amino propiophenone prepared as above (11.8 g, 0.048 mol) was dissolved in 120 ml of methanol, and stirred for 10 min. The temperature was maintained at 10~20 by cooling in water bath, and sodium borohydride (1.90 g, 0.050 mol) was added to the reaction mixture in proportions. After the completion of the addition, a react was allowed to proceed at room temperature for 1 hour. The reaction mixture was adjusted to pH of 7 with 2N hydrochloric acid, and evaporated under reduced pressure to remove methanol. 50 ml of water was added, and the mixture was then adjusted to pH of >9 with 10% sodium hydroxide (w/w), and extracted with ethyl acetate (100 ml×2). The organic phases were combined, washed with saturated brine, dried, and evaporated to remove the solvent, obtaining 11.8 g of (R)—N-trifluoroacetyl-2-amino phenyl propanol. The yield was 99%.

5) Preparation of (R)-2-aminophenyl propanol hydrochloride (R)—N-trifluoroacetyl-2-amino phenyl propanol (11.8 g, 0.0477 mol) prepared as above was dissolved in 100 ml of isopropanol. At a controlled temperature of <10 with ice bath, 70 ml of concentrated hydrochloric acid was added dropwise. The temperature was slowly raised to 40, and a reaction was allowed to proceed for 15 hours. The solvent was removed by evaporation under reduced pressure (water bath temperature <60), and benzene (100 ml×2) was added to remove water by azeotropism. Ethanol (120 ml×2) was then added for the azeotropism. A white solid was obtained by evaporation till dry. The solid was recrystallized with ethanol, and dried, to produce 6.7 g of (R)-2-amino phenyl propanol hydrochloride. The yield was 74.9%.

6) Preparation of (1R,2R)-1-phenyl-2-(4-(2-methoxyphenyl)piperazinyl)propan-1-ol hydrochloride and (1S,2R)-1-phenyl-2-(4-(2-methoxyphenyl)piperazinyl)propan-1-ol hydrochloride (R)-2-amino phenyl propanol hydrochloride (5.63 g, 0.03 mol) prepared as above, N,N-bis-(2-chloroethyl)-2-methoxyaniline (7.44 g, 0.03 mol), sodium bicarbonate (2.52 g, 0.03 mol), and sodium carbonate (3.18 g, 0.03 mol) were added to 160 ml of anhydrous ethanol, and a reaction under refluxing was allowed to proceed for 15 hours at an elevated temperature. The reaction mixture was cooled, and filtered to remove inorganic salts. The filtrate was evaporated till dry under reduced pressure, to obtain oily product. The oily product was purified by neutral alumina column chromatography, and eluted with dichloromethane/methanol, to obtain (1S, 2R)-1-phenyl-2-(4-(2-methoxyphenyl)piperazinyl)propan-1-ol (III-1), which was dissolved in 15 ml of ethyl acetate, and acidified with HCl/C$_2$H$_5$OH (5N) to form a salt, and the salt was filtered, dried, and then recrystallized with ethanol, obtaining 0.46 g of product having a melting point of 218 to 220° C., with a yield of 4.22%. The purification gave (1R, 2R)-1-phenyl-2-(4-(2-methoxyphenyl)piperazinyl)propan-1-ol (III-2), which was dissolved in 80 ml of ethyl acetate, acidified with HCl/C$_2$H$_5$OH (5N) to form a salt, and the salt was filtered, dred, and then recrystallized with ethanol, obtaining 4.82 g of product having a melting point of 236 to 238° C., with a yield of 44.3%.

(1R,2R)-1-phenyl-2-(4-(2-methoxyphenyl)piperazinyl)propan-1-ol hydrochloride $^1$HNMR (DMSO-d$_6$): δ1.01 (d, 3H, J=6.8 Hz), 3.11-3.65 (m, 9H, A-H, NCH), 3.80 (s, 3H, OCH3), 4.73 (d, 1H, J=10.0 Hz, CHOH), 6.91-7.03 (m, 4H, Ar—H), 7.35-7.43 (m, 5H, Ar—H), 9.63 (br, 1H, HCl)
MS: m/z 326.2 (M$^+$)
[α]D20=−43.1°

(1R,2R)-1-phenyl-2-(4-(2-methoxyphenyl)piperazinyl)propan-1-ol hydrochloride $^1$HNMR (DMSO-d$_6$): δ1.06 (d, 3H, J=6.8 Hz), 3.17-3.79 (m, 9H, AH, NCH), 3.80 (s, 3H, OCH3), 5.54 (s, 1H, CHOH), 6.89-7.04 (m, 4H, Ar—H), 7.28 (t, 1H, J=7.2 Hz), 7.38 (t, 2H, J=7.2 Hz), 7.45 (m, 2H, J=7.2 Hz), 10.72 (br, 1H, HCl)
MS: m/z 326.2 (M$^+$)
[α]D20=−4.3°.

Example 16

Preparation of (1RS,2SR)-5-(1-hydroxy-2-(4-(2-methoxyphenyl)piperazin-1-yl)propyl)indolin-2-one (IV-1) hydrochloride and (1RS,2RS)-5-(1-hydroxy-2-(4-(2-methoxyphenyl)piperazin-1-yl)propyl)indolin-2-one (IV-2) hydrochloride 5-(2-chloropropyl)-indolin-2-one was prepared from indolin-2-one according to the synthetic and working-up method of general procedure B. 5-(2-chloropropyl)-indolin-2-one (2.46 g, 0.011 mol) and 2-methoxyphenyl piperazine (1.92 g, 0.01 mol) were dissolved in 100 ml of acetonitrile, and triethyl amine (3.04 g, 0.03 mol) was added. A reaction under refluxing was allowed to proceed at an elevated temperature for 3 hours. Working up according to general procedure B gave 3.66 g of 5-(2-(4-(2-methoxyphenyl)piperazin-1-yl) propanoyl)indolin-2-one hydrochloride. The yield was 88.0%.

The 5-(2-(4-(2-methoxyphenyl)piperazin-1-yl)propanoyl) indolin-2-one hydrochloride (1.66 g, 4 mmol) was dissolved in 50 ml of methanol solution, and sodium borohydride (0.15 g, 8.4 mmol) was added in proportions, mixed and stirred at room temperature for 3 hours. Working up according to general procedure B gave 0.55 g of (1RS,2SR)-5-(1-hydroxy-2-

(4-(2-methoxyphenyl)piperazin-1-yl)propyl)indolin-2-one (IV-1) hydrochloride having a melting point of 213 to 215° C., with a yield of 32.9%; and 0.51 g of (1RS,2RS)-5-(1-hydroxy-2-(4-(2-methoxyphenyl)piperazin-1-yl)propyl)indolin-2-one (IV-2) hydrochloride having a melting point of 237 to 239° C., with a yield of 30.5%.

(1RS,2SR)-5-(1-hydroxy-2-(4-(2-methoxyphenyl) piperazin-1-yl)propyl)indolin-2-one hydrochloride $^1$HNMR (DMSO-d$_6$): δ1.01 (d, 3H, J=6.8 Hz), 2.82-3.75 (m, 11H), 3.81 (s, 3H, OCH3), 4.61 (d, 1H, J=10.0 Hz), 6.73-7.30 (m, 7H, Ar—H), 9.69 (br, 1H, HCl), 10.21 (s, 1H, CONH)
MS: m/z 381.2 (M$^+$)

(1RS,2RS)-5-(1-hydroxy-2-(4-(2-methoxyphenyl) piperazin-1-yl)propyl)indolin-2-one hydrochloride $^1$HNMR (DMSO-d$_6$): δ1.08 (d, 3H, J=6.8 Hz), 2.79-3.78 (m, 11H), 3.80 (s, 3H, OCH3), 5.51 (s, 1H), 6.83-7.31 (m, 7H, Ar—H), 10.13 (s, 1H, CONH), 11.02 (br, 1H, HCl)
MS: m/z 381.2 (M$^+$)

Example 17

Preparation of (1RS,2SR)-5-(1-hydroxy-2-(4-(2-methoxyphenyl)piperazin-1-yl)propyl)-1H-benzo[d]imidazol-2(3H)-one (IV-3) hydrochloride and (1RS, 2RS)-5-(1-hydroxy-2-(4-(2-methoxyphenyl) piperazin-1-yl)propyl)-1H-benzo[d]imidazol-2(3H)-one (IV-4) hydrochloride 5-(2-chloropropyl)-1H-benzimidazol-2-one was prepared from 1H-benzimidazol-2-one according to the synthetic and working-up method of general procedure B. 5-(2-chloropropyl)-1H-benzimidazol-2-one (2.47 g, 0.011 mol) and 2-methoxyphenyl piperazine (1.92 g, 0.01 mol) were dissolved in 100 ml of acetonitrile, and triethylamine (3.04 g, 0.03 mol) was added. A reaction under refluxing was allowed to proceed for 3 hours at an elevated temperature. Working up according to general procedure B gave 3.73 g of 5-(2-(4-(2-methoxyphenyl)piperazin-1-yl)propanoyl)-1H-benzo[d]imidazol-2(3H)-one hydrochloride. The yield was 89.5%.
The 5-(2-(4-(2-methoxyphenyl)piperazin-1-yl)propanoyl)-1H-benzo[d]imidazol-2(3H)-one hydrochloride (1.67 g, 4 mmol) was dissolved in 50 ml of methanol solution, and sodium borohydride (0.15 g, 8.4 mmol) was added in proportions, mixed and stirred at room temperature for 3 hours. Working up according to general procedure B gave 0.57 g of (1RS, 2SR)-5-(1-hydroxy-2-(4-(2-methoxyphenyl)piperazin-1-yl)propyl)-1H-benzo[d]imidazol-2(3H)-one (IV-3) hydrochloride having a melting point of 221 to 223° C., with a yield of 34.0%; and 0.50 g of (1RS,2RS)-5-(1-hydroxy-2-(4-(2-methoxyphenyl)piperazin-1-yl)propyl)-1H-benzo[d]imidazol-2(3H)-one (IV-4) hydrochloride having a melting point of 242 to 244° C., with a yield of 29.8%.

(1RS,2SR)-5-(1-hydroxy-2-(4-(2-methoxyphenyl) piperazin-1-yl)propyl)-1H-benzo[d]imidazol-2(3H)-one hydrochloride $^1$HNMR (DMSO-d$_6$): δ1.00 (d, 3H, J=6.8 Hz), 2.62-3.95 (m, 11H), 3.81 (s, 3H, OCH3), 4.67 (d, 1H, J=10.0 Hz), 6.03-7.30 (m, 9H, Ar—H), 9.96 (br, 1H, HCl)
MS: m/z 382.2 (M$^+$)

(1RS,2RS)-5-(1-hydroxy-2-(4-(2-methoxyphenyl) piperazin-1-yl)propyl)-1H-benzo[d]imidazol-2(3H)-one hydrochloride $^1$HNMR (DMSO-d$_6$): δ1.07 (d, 3H), 2.53-3.87 (m, 11H), 3.83 (s, 3H, OCH3), 5.53 (s, 1H), 6.01-7.31 (m, 9H, Ar—H), 11.13 (br, 1H, HCl)
MS: m/z 382.2 (M$^+$).

Example 18

Preparation of (1RS,2SR)-6-(1-hydroxy-2-(4-(3-(trifluoromethyl)phenyl)piperazin-1-yl)propyl)benzo[d]thiazol-2(3H)-one (IV-5) hydrochloride and (1RS, 2RS)-6-(1-hydroxy-2-(4-(3-(trifluoromethyl)phenyl) piperazin-1-yl)propyl)benzo[d]thiazol-2(3H)-one (IV-6) hydrochloride 6-(2-chloropropyl)-3H-benzothiazol-2-one was prepared from 3H-benzothiazol-2-one according to the synthetic and working-up method of general procedure B. 6-(2-chloropropyl)-3H-benzothiazol-2-one (2.66 g, 0.011 mol) and 3-trifluoromethylphenyl piperazine (2.30 g, 0.01 mol) were dissolved in 100 ml of acetonitrile, and triethylamine (3.04 g, 0.03 mol) was added. A reaction under refluxing was allowed to proceed for 3 hours at an elevated temperature. Working up according to general procedure B gave 4.10 g of 6-(2-(4-(3-(trifluoromethyl)phenyl)piperazin-1-yl)propanoyl)benzo[d]thiazol-2(3H)-one hydrochloride. The yield was 86.9%.

The 6-(2-(4-(3-(trifluoromethyl)phenyl)piperazin-1-yl)propanoyl)benzo[d]thiazol-2(3H)-one hydrochloride (1.89 g, 4 mmol) was dissolved in 50 ml of methanol solution, and sodium borohydride (0.15 g, 8.4 mmol) was added in proportions, mixed and stirred at room temperature for 3 hours. Working up according to general procedure B gave 0.61 g of (1RS, 2SR)-6-(1-hydroxy-2-(4-(3-(trifluoromethyl)phenyl) piperazin-1-yl)propyl)benzo[d]thiazol-2(3H)-one (IV-5) hydrochloride having a melting point of 217 to 219° C., with a yield of 32.2%; and 0.57 g of (1RS,2RS)-6-(1-hydroxy-2-(4-(3-(trifluoromethyl)phenyl)piperazin-1-yl)propyl)benzo[d]thiazol-2(3H)-one (IV-6) hydrochloride having a melting point of 235 to 237° C., with a yield of 30%.

(1RS,2SR)-6-(1-hydroxy-2-(4-(3-(trifluoromethyl) phenyl)piperazin-1-yl)propyl)benzo[d]thiazol-2(3H)-one hydrochloride $^1$HNMR (DMSO-d$_6$): δ1.01 (d, 3H, J=6.8 Hz), 2.59-3.99 (m, 11H), 4.65 (d, 1H, J=10.0 Hz), 6.28-8.34 (m, 8H, Ar—H), 10.04 (br, 1H, HCl)
MS: m/z 437.1 (M$^+$)

(1RS,2RS)-6-(1-hydroxy-2-(4-(3-(trifluoromethyl) phenyl)piperazin-1-yl)propyl)benzo[d]thiazol-2(3H)-one hydrochloride $^1$HNMR (DMSO-d$_6$): δ1.09 (d, 3H, J=6.8 Hz), 2.44-3.96 (m, 11H), 5.52 (br, 1H), 6.31-8.43 (m, 8H, Ar—H), 11.18 (br, 1H, HCl)

MS: m/z 437.1 (M+)

Example 19

| Tablet: compound prepared in Example 1 | 25 mg |
|---|---|
| Sucrose | 155 mg |
| Corn starch | 65 mg |
| Magnesium stearate | 5 mg |

Preparation: the compound prepared in Example 1, as the active ingredient, was mixed with sucrose and corn starch, wetted with water, mixed well with stirring, dried, crushed and screened. Magnesium stearate was then added and mixed well, and the mixture was press into tablets. Each tablet weighed 250 mg, with the active ingredient content of 25 mg.

Example 20

| Injection: compounds prepared in Example 8 | 10 mg |
|---|---|
| Water for injection | 990 mg |

Preparation: the active ingredient was dissolved in water for injection, mixed well and filtered. The obtained solution was aliquoted into ampoule vials under sterile condition. Each vial contained 100 mg of the solution, with the active ingredient content of 1 mg/vial.

Example 21

Acetic Acid-Induced Abdominal Writhing Test in Mice

1. Experimental Animals:
Kunming mice, SPF KM mice purchased from SHANGHAI SLAC LABORATORY ANIMAL CO. LTD and kept in normal environment.
2. Modes of Administration
The compounds were dissolved in water for injection at a concentration of 4 mg/ml, 2 mg/ml and 1 mg/ml and were given intragastrically to animals.
3. Doses
Three different doses (10, 20, and 40 mg/kg) were administered to the test groups.
4. Test Method
Aspirin was used as a positive control and acetic acid writhing test was used.
5. Experimental Protocol
30 mice (half male and half female) weighing 18-23 g were divided into five groups, including negative control group, positive control group, low dose group, medium dose group and high dose group:

| negative control group | physiological saline | 20 ml/kg |
|---|---|---|
| positive control group | aspirin | 200 mg/kg |
| low dose group | test drug | 10 mg/kg |
| medium dose group | test drug | 20 mg/kg |
| high dose group | test drug | 40 mg/kg |

Mice in test group received test drug (10 mg/kg, 20 mg/kg, 40 mg/kg) via intragastric administration. Negative control group received physiological saline (20 ml/kg) via oral administration. Positive control group received aspirin (200 mg/kg) via oral administration. One hour later, each group received 0.7% acetic acid 10 ml/kg intraperitoneally. Five minutes later, the number of writhes was counted within the subsequent 15 min period; inhibition percentage of writhing response in each test group was calculated by the following equation:

$$\text{Inhibition percentage} = \frac{\begin{array}{c}\text{average number of writhes in}\\ \text{negative control group} -\\ \text{average number of writhes}\\ \text{in treatment group}\end{array}}{\begin{array}{c}\text{average number of writhes}\\ \text{in negative control group}\end{array}} \times 100\%$$

6. Results of the Multiple Dose Administration for Some Compounds were Shown in Table 3.

TABLE 3

Screening results in acetic-acid writhing test in mice

| | Dose | | | | |
|---|---|---|---|---|---|
| | Inhibition percentage of writhing response (%) | | | | |
| Compounds | Aspirin 200 mg/kg | 10 mg/kg | 20 mg/kg | 40 mg/kg | Notes |
| I-1 | 95.05 ** | 64.38 * | 68.13 * | 83.13 ** | Ig |
| I-2 | 95.05 ** | 40.53 | 63.16 * | 68.95 * | Ig |
| I-3 | 95.05 ** | 49.61 | 76.38 * | 83.46 ** | Ig |
| I-4 | 95.05 ** | 35.00 | 49.38 * | 78.13 ** | Ig |
| I-7 | 95.05 ** | 61.02 | 75.42 ** | 70.34 * | Ig |
| I-13 | 95.05 ** | 73.33 * | 84.55 * | 87.88 ** | Ig |
| I-14 | 95.05 ** | 74.55 * | 79.39 * | 76.36 | Ig |
| I-20 | 95.05 ** | 46.61 | 72.03 * | 64.41 | Ig |
| II-1 | 95.05 ** | 30.09 | 47.79 * | 58.41 * | Ig |
| II-2 | 95.05 ** | 69.91 * | 71.48 * | 74.34 ** | Ig |
| III-1 | 95.05 ** | 69.28 ** | 55.56 * | 67.32 ** | Ig |
| III-2 | 95.05 ** | 64.05 ** | 76.47 ** | 86.27 ** | Ig |
| IV-1 | 95.05 ** | 92.92 ** | 74.34 * | 89.38 ** | Ig |
| IV-2 | 95.05 ** | 98.23 ** | 97.35 ** | 93.81 ** | Ig |

Note:
* $p < 0.05$,
** $p < 0.01$ VS negative control group

Example 22

Hot-Plate Test in Mice

1. Experimental Animals
Kunming mice, SPF KM mice were purchased from SHANGHAI SLAC LABORATORY ANIMAL CO. LTD and kept in normal environment.
2. Modes of Administration
The compounds were dissolved in water for injection at a concentration of 4 mg/ml, 2 mg/ml and 1 mg/ml and were given subcutaneously to animals.
3. Doses
Three different doses (10, 20, and 40 mg/kg) were administered to the test groups.
4. Test Method
Morphine was used as a positive control and hot plate test was used.
5. Experimental Protocol
30-40 mice (half male and half female) weighing 18-23 g were used. First, each mouse was placed on a hot plat at 55° C. to determine basic pain threshold for 2-3 times. Those animals with basic pain threshold of 5-30 s were qualified, unqualified mice were not used. 30 qualified mice were divided into five groups, including negative control group, positive control group, low-dose group, medium-dose group and high-dose group:

| negative control group | directly determine the basic pain threshold | |
|---|---|---|
| positive control group | morphine | 0.2 mg/ml 0.2 ml |
| low-dose group | test drug | 1 mg/ml 0.2 ml |
| median-dose group | test drug | 2 mg/ml 0.2 ml |
| high-dose group | test drug | 4 mg/ml 0.2 ml |

Mice in test groups received test sample solution (10 mg/kg, 20 mg/kg, 40 mg/kg) via subcutaneous injection in the neck. Positive control group received subcutaneous injection of morphine (2 mg/kg). One hour later, pain threshold values were determined for mice in each group as post-drug pain threshold. Percentage increase in pain threshold was calculated according to the following equation:

$$\text{Percentage increase in pain threshold \%} = \frac{\text{pain threshold after treatment} - \text{average basic pain threshold}}{\text{average basic pain threshold}} \times 100\%.$$

6. Results for Some Compounds were Shown in Table 4.

TABLE 4

Screening results in hot plate test in mice

| | Dose | | | | |
|---|---|---|---|---|---|
| | Percentage increase in pain threshold (%) | | | | |
| Compound | 2 mg/kg morphine | 10 mg/kg | 20 mg/kg | 40 mg/kg | Notes |
| I-1 | 202.5 ** | 4.53 | 11.7 | 89.62 ** | S.c. |
| I-13 | 202.5 ** | 16.19 | 74.59 * | 142.41 ** | S.c. |
| I-17 | 202.5 ** | 59.02 | 147.36 ** | 172.27 ** | S.c. |
| I-20 | 202.5 ** | 63.29 * | 80.88 * | 186.25 ** | S.c. |
| III-2 | 202.5 ** | 72.91 | 133.48 * | 151.86 * | S.c. |

Note:
* $p < 0.05$,
** $p < 0.01$ VS negative control group;
S.c: subcutaneous

Example 23

Competitive Binding Between the Compounds and Opioid Receptor Subtypes μ, δ, κ

Competitive binding between the compounds and opioid receptor subtypes μ, δ, κ was determined by radioactive ligand binding assay to verify that such compounds had non-opioid analgesic pathway.

Competitive binding assay was performed in overall binding tube, non-specific binding tube and sample tube respectively. 30 ng membrane protein, and [3H]Diprenorphine (final concentration of 0.4 nM) were added to the overall binding tube and the volume was adjusted to 200 μL, with 50 mM Tris-HCl (pH7.4). 10 μM Naloxone was additionally added to the corresponding non-specific binding tube. The respective test compounds were added to the sample tube (final concentration of $10^{-5}$ M), incubated at 37° C. for 30 min and placed in ice bath to terminate the reaction. The reaction mixture was filtered through GF/C(Whatman) glass fiber filter by vacuum filtration on a Millipore sample collector. The filter was washed three times with 50 mM Tris-HCl (pH7.4), each with 4 ml; dried and transferred into a 0.5 ml Eppendorf tube, in which 0.5 ml lipophilic scintillation fluid was added. Radioactivity was detected by a LS6500 scintillation counter. Each concentration had three duplicate test tubes and each separate test was repeated 3 to 4 times.

Specific binding CMP value for each sample tube=overall binding CPM value for each sample tube-CPM value of non-specific binding tube.

[Inhibition percentage of competitive binding between the test compound and different opioid receptor subtypes (%)=(100%−specific binding (*CPM* value) of sample tube/specific binding (*CPM* value) of solvent group×100%)]

Average was taken for each test drug from three duplicate tubes; each test was repeated two or more times. Data were presented as mean±SE and statistical comparison was made by ANOVA. None of the 4 tested compounds showed high affinity to the three different opioid receptor subtypes. Results were shown in Table 5.

TABLE 5

The affinity of compounds to opioid receptor subtypes μ, δ and κ

| Compound | Test concentration (mol/L) | μ (%) | δ (%) | κ (%) |
|---|---|---|---|---|
| Naloxone | $10^{-6}$ | 100 | 100 | 100 |
| I-1 | $10^{-5}$ | 22.7 ± 2.2 | 0 | 2.7 ± 0.9 |
| I-20 | $10^{-5}$ | 13.4 ± 2.1 | 0 | 8.9 ± 0.2 |
| II-2 | $10^{-5}$ | 5.3 ± 0.9 | 12.8 ± 0.8 | 36.5 ± 1.6 |
| III-2 | $10^{-5}$ | 25.1 ± 1.3 | 16.8 ± 2.3 | 40.0 ± 0.6 |
| IV-1 | $10^{-5}$ | 7.6 ± 0.8 | 0 | 5.3 ± 0.1 |

Example 24

Studies of Acute Toxicity of the Compound I-1 and I-20

For compound I-1, a sequential test for boundary determination was conducted ("Drug safety evaluation", Shayene C Gad, translated by Fan Yuming et al., first edition, Chemical Industry Press, 2006, 110-140.) The po $LD_{50}$ of mice is greater than 2000 mg/kg.

For statistics of I-20, Bliss method was used ("Experimental Design and Statistical Basis for Drug Evaluation", Changxiao Liu, Ruiyuan Su, first edition, Military Medical Science Press, 1993, 80-90). The po $LD_{50}$ of mice is 674 mg/kg.

Example 25

Bacterial Reverse Mutation Test on I-20

Bacterial reverse mutation test on compound I-20 was performed on *Salmonella typhimurium* histidine auxotroph mutants TA97, TA98, TA100 and TA102 (purchased from MolTox company) using conventional procedures of Ames test.

Observation period: colony counting was done 48 hours after cultivation at 37° C.

Drug solutions with different concentrations were prepared with double distilled water, and the doses were 5, 50, 500, 1000, 5000 μg/plate.

Direct effect of the test drug in the absence of metabolic activity was determined by standard plate incorporation assay. The composition of the test top layer was: 2.0 ml top layer, 0.1 ml drug solution, 0.1 ml bacteria solution and 0.5 ml phosphate buffer.

Pre-incubation was used in the determination of the drug's mutagenic effect in the presence of metabolic activity. The composition of the test top layer is: 2.0 ml top layer, 0.1 ml drug solution, 0.1 ml bacteria solution and 0.5 ml $S_9$ mix.

The resulting drug solution, bacterial solution and S9 mix were first incubated at 35° C. for 30 min while shaking, and then tested according to standard plate incorporation assay. Each dose was tested in three plates, each mutant was tested in the absence or presence of metabolic activity ($-S_9$ or $+S_9$) and repeated twice, the number of revertant colonies was calculated as x±SD.

Results: the test included two parts, $-S_9$ and $+S_9$. TA98 in $-S_9$ test system and TA97 in $+S_9$ test system had bacteristatic effects. Other doses had no bacteristatic effect to all strains, and the background growth was good. None of the tested dose resulted in significant increase in the number of revertant colonies either in $-S_9$ system or in $+S_9$ system. Consequently, Ames test exhibited negative.

The results described above indicate that the compound I-20 have obvious analgesic effect and can be well absorbed via oral administration. I-20 has no obvious affinity to opioid receptor subtypes μ, δ, κ, indicating its non-opioid analgesic pathway. With negative result in Ames test and high therapeutic index, I-20 has the potential to be developed as a novel non-opioid analgesic.

What is claimed is:

1. A substituted phenylpiperazine aryl alkanol derivative having the following general formula:

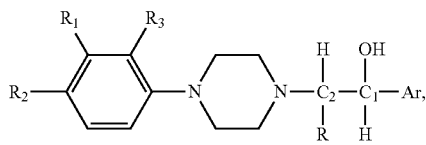

wherein:
R represents $C_1$-$C_5$ alkyl unsubstituted or substituted with one to three fluorine, amino or hydroxyl;
$R_1$, $R_2$ and $R_3$ each represent H, F, Cl unsubstituted or one to three fluorine substituted $C_1$-$C_3$ alkyl, or unsubstituted or one to three fluorine substituted $C_1$-$C_3$ alkoxy, with a proviso that $R_1$, $R_2$ and $R_3$ are not simultaneously H,
Ar represents one of the following groups:

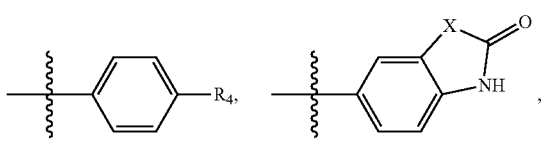

wherein:
$R_4$ represents H, F, hydroxyl, methoxy, ethoxy, trifluoromethoxy, —NHCOCH$_3$, —NHSO$_2$CH$_3$ or —NHSOCH$_3$;
X represents CH$_2$, S or NH;
with a proviso that: $C_1$ and $C_2$ in the general formula represent chiral carbon atoms, and the compound is one of the (1RS, 2SR), (1RS, 2RS), (1R, 2S), (1S, 2S), (1R, 2R) or (1S, 2R) isomers; or a salt thereof.

2. The substituted phenylpiperazine aryl alkanol derivative according to claim 1, wherein R represents unsubstituted or fluorine substituted $C_1$-$C_4$ alkyl.

3. A substituted phenylpiperazine aryl alkanol derivative having the following general formula:

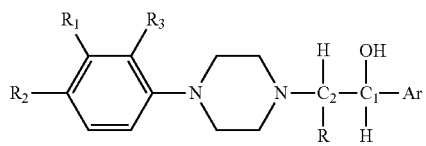

wherein:
$R_1$, $R_2$ and $R_3$ each represent F or Cl;
R represents $C_1$-$C_5$ alkyl unsubstituted or substituted with one to three fluorine, amino or hydroxyl;
Ar represents one of the following groups:

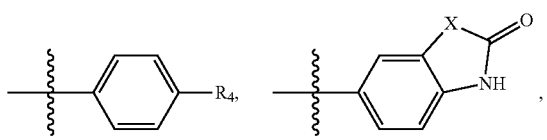

wherein:
$R_4$ represents H, F, hydroxyl, methoxy, ethoxy, trifluoromethoxy, —NHCOCH$_3$, —NHSO$_2$CH$_3$ or —NHSOCH$_3$;
X represents CH$_2$, S or NH;
with a proviso that: $C_1$ and $C_2$ in the general formula represent chiral carbon atoms, and the compound is one of the (1RS, 2SR), (1RS, 2RS), (1R, 2S), (1S, 2S), (1R, 2R) or (1S, 2R) isomers; or a salt thereof.

4. A substituted phenylpiperazine aryl alkanol derivative having the following formula:

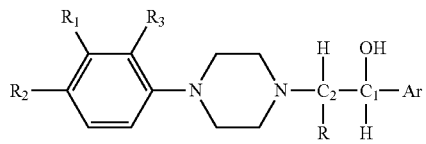

wherein:
$R_1$, $R_2$ and $R_3$ each represent unsubstituted or one to three fluorine substituted $C_1$-$C_3$ alkyl;
R represents $C_1$-$C_5$ alkyl unsubstituted or substituted with one to three fluorine, amino or hydroxyl;
Ar represents one of the following groups:

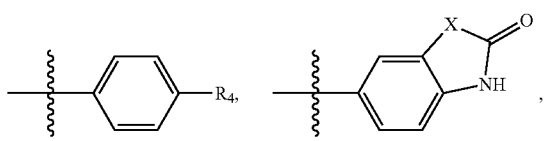

wherein:
R₄ represents H, F, hydroxyl, methoxy, ethoxy, trifluoromethoxy, —NHCOCH₃, —NHSO₂CH₃ or —NHSOCH₃;
X represents CH₂, S or NH;
with a proviso that: $C_1$ and $C_2$ in the general formula represent chiral carbon atoms, and the compound is one of the (1RS, 2SR), (1RS, 2RS), (1R, 2S), (1S, 2S), (1R, 2R) or (1S, 2R) isomers; or a salt thereof.

5. The substituted phenylpiperazine aryl alkanol derivative according to claim 1, wherein $R_1$, $R_2$ and $R_3$ each represent unsubstituted $C_1$-$C_3$ alkoxy.

6. The substituted phenylpiperazine aryl alkanol derivative according to claim 1, wherein the salt is hydrochloride, hydrobromide salt, sulfate, trifluoroacetate or methanesulfonate.

7. The substituted phenylpiperazine aryl alkanol derivative according to claim 1, being a compound selected from the group consisting of:
(1RS,2SR)-1-phenyl-2-(4-(3-trifluoromethylphenyl)piperazinyl)-propan-1-ol,
(1RS,2RS)-1-phenyl-2-(4-(3-trifluoromethylphenyl)piperazinyl)-propan-1-ol,
(1RS,2SR)-1-phenyl-2-(4-(3-chlorophenyl)piperazinyl)-propan-1-ol,
(1RS,2RS)-1-phenyl-2-(4-(3-chlorophenyl)piperazinyl)-propan-1-ol,
(1RS,2SR)-1-phenyl-2-(4-(2,3-dimethylphenyl)piperazinyl)-propan-1-ol,
(1RS,2RS)-1-phenyl-2-(4-(2,3-dimethylphenyl)piperazinyl)-propan-1-ol,
(1RS,2SR)-1-phenyl-2-(4-(4-methoxyphenyl)piperazinyl)-propan-1-ol,
(1RS,2RS)-1-phenyl-2-(4-(4-methoxyphenyl)piperazinyl)-propan-1-ol,
(1RS,2SR)-1-phenyl-2-(4-(3-methoxyphenyl)piperazinyl)-propan-1-ol,
(1RS,2RS)-1-phenyl-2-(4-(3-methoxyphenyl)piperazinyl)-propan-1-ol,
(1RS,2SR)-1-(4-fluorophenyl)-2-(4-(2-methoxyphenyl)piperazinyl)-propan-1-ol,
(1RS,2RS)-1-(4-fluorophenyl)-2-(4-(2-methoxyphenyl)piperazinyl)-propan-1-ol,
(1RS,2SR)-1-(4-methoxyphenyl)-2-(4-(2-methoxyphenyl)piperazinyl)-propan-1-ol,
(1RS,2RS)-1-(4-methoxyphenyl)-2-(4-(2-methoxyphenyl)piperazinyl)-propan-1-ol,
(1RS,2SR)-1-(4-acetylaminophenyl)-2-(4-(3-trifluoromethylphenyl)piperazinyl)-propan-1-ol,
(1RS,2RS)-1-(4-acetylaminophenyl)-2-(4-(3-trifluoromethylphenyl)piperazinyl)-propan-1-ol,
(1RS,2SR)-1-(4-methanesulfonamido phenyl)-2-(4-(3-trifluoromethylphenyl)piperazinyl)-propan-1-ol,
(1RS,2RS)-1-(4-methanesulfonamido phenyl)-2-(4-(3-trifluoromethylphenyl)piperazinyl)-propan-1-ol,
(1RS,2SR)-1-phenyl-2-(4-(2-methoxyphenyl)piperazinyl)-propan-1-ol,
(1RS,2RS)-1-phenyl-2-(4-(2-methoxyphenyl)piperazinyl)-propan-1-ol,
(1RS,2SR)-1-phenyl-2-(4-(2-methoxyphenyl)piperazinyl)-butan-1-ol,
(1RS,2RS)-1-phenyl-2-(4-(2-methoxyphenyl)piperazinyl)-butan-1-ol,
(1RS,2SR)-1-phenyl-2-(4-(2-methoxyphenyl)piperazinyl)-pentan-1-ol,
(1RS,2RS)-1-phenyl-2-(4-(2-methoxyphenyl)piperazinyl)-pentan-1-ol,
(1RS,2SR)-1-phenyl-2-(4-(2-methoxyphenyl)piperazinyl)-hexan-1-ol,
(1RS,2RS)-1-phenyl-2-(4-(2-methoxyphenyl)piperazinyl)-hexan-1-ol,
(1R,2S)-1-phenyl-2-(4-(2-methoxyphenyl)piperazinyl)-propan-1-ol,
(1S,2S)-1-phenyl-2-(4-(2-methoxyphenyl)piperazinyl)-propan-1-ol,
(1S,2R)-1-phenyl-2-(4-(2-methoxyphenyl)piperazinyl)-propan-1-ol,
(1R,2R)-1-phenyl-2-(4-(2-methoxyphenyl)piperazinyl)-propan-1-ol,
(1RS,2SR)-5-(1-hydroxy-2-(4-(2-methoxyphenyl)piperazin-1-yl)propyl)indolin-2-one,
(1RS,2RS)-5-(1-hydroxy-2-(4-(2-methoxyphenyl)piperazin-1-yl)propyl)indolin-2-one,
(1RS,2SR)-5-(1-hydroxy-2-(4-(2-methoxyphenyl)piperazin-1-yl)propyl)-1H-benzo[d]imidazol-2(3H)-one,
(1RS,2RS)-5-(1-hydroxy-2-(4-(2-methoxyphenyl)piperazin-1-yl)propyl)-1H-benzo[d]imidazol-2(3H)-one,
(1RS,2SR)-6-(1-hydroxy-2-(4-(3-(trifluoromethyl)phenyl)piperazin-1-yl)propyl)benzo[d]thiazol-2(3H)-one, and
(1RS,2RS)-6-(1-hydroxy-2-(4-(3-(trifluoromethyl)phenyl)piperazin-1-yl)propyl)benzo[d]thiazol-2(3H)-one,
or a salt or a hydrate thereof.

8. A substituted phenylpiperazine aryl alkanol derivative selected from the group consisting of:
(1RS,2SR)-1-phenyl-2-(4-(3-trifluoromethylphenyl)piperazinyl)-propan-1-ol,
(1RS,2SR)-1-(4-methoxyphenyl)-2-(4-(2-methoxyphenyl)piperazinyl)-propan-1-ol,
(1RS,2RS)-1-phenyl-2-(4-(2-methoxyphenyl)piperazinyl)-propan-1-ol, and
(1R,2R)-1-phenyl-2-(4-(2-methoxyphenyl)piperazinyl)-propan-1-ol,
or a salt thereof.

9. The substituted phenylpiperazine aryl alkanol derivative according to claim 1, wherein R represents $C_1$-$C_4$ alkyl.

10. The substituted phenylpiperazine aryl alkanol derivative according to claim 1, wherein $R_1$, $R_2$ and $R_3$ each represent fluorine, chlorine, methyl, trifluoromethyl, or methoxy.

11. A pharmaceutical composition, comprising a therapeutically effective amount of a substituted phenylpiperazine aryl alkanol derivative according to claim 1, its salt, and a pharmaceutically acceptable carrier.

12. A method of treating pain in mammals, comprising administrating a substituted phenylpiperazine aryl alkanol derivative having the following general formula, to individuals with such need:

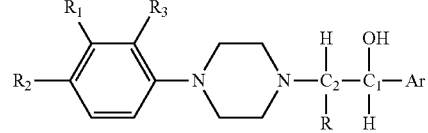

wherein:
R represents $C_1$-$C_5$ alkyl unsubstituted or substituted with one to three fluorine, amino or hydroxyl;
$R_1$, $R_2$ and $R_3$ each represent H, F, Cl, unsubstituted or one to three fluorine substituted $C_1$-$C_3$ alkyl, or unsubstituted or one to three fluorine substituted $C_1$-$C_3$ alkoxy, with a proviso that $R_1$, $R_2$ and $R_3$ are not simultaneously H, Ar represents one of the following groups:

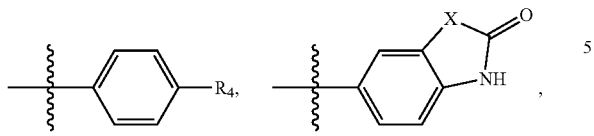

wherein:
R$_4$ represents H, F, hydroxyl, methoxy, ethoxy, trifluoromethoxy, —NHCOCH$_3$, —NHSO$_2$CH$_3$ or —NHSOCH$_3$;
X represents CH$_2$, S or NH;
with a proviso that: C$_1$ and C$_2$ in the general formula represent chiral carbon atoms, and the compound is one of the (1RS, 2SR), (1RS, 2RS), (1R, 2S), (1S, 2S), (1R, 2R) or (1S,2R) isomers; and or a salt and hydrate thereof.

13. The method according to claim 12, wherein the pain is selected from the group consisting of nociceptive pain, acute pain, chronic pain, neuropathic pain, psychogenic pain and mixed pain.

* * * * *